United States Patent
Yen et al.

(10) Patent No.: US 9,260,363 B2
(45) Date of Patent: *Feb. 16, 2016

(54) INDENOTRIPHENYLENE DERIVATIVES AND ORGANIC LIGHT EMITTING DEVICE USING THE SAME

(71) Applicant: LUMINESCENCE TECHNOLOGY CORPORATION, Hsinchu County (TW)

(72) Inventors: Feng-Wen Yen, Hsinchu County (TW); Cheng-Hao Chang, Hsinchu County (TW); Hsu-Kai Chang, Hsinchu County (TW); Feng-Ying Wang, Hsinchu County (TW)

(*) Notice: Subject to any disclaimer, the term of this patent is extended or adjusted under 35 U.S.C. 154(b) by 350 days.

This patent is subject to a terminal disclaimer.

(21) Appl. No.: 13/674,099

(22) Filed: Nov. 12, 2012

(65) Prior Publication Data
US 2014/0131664 A1 May 15, 2014

(51) Int. Cl.
*H01L 51/50* (2006.01)
*C07C 13/62* (2006.01)
(Continued)

(52) U.S. Cl.
CPC .............. *C07C 13/62* (2013.01); *C07D 221/18* (2013.01); *C07D 471/04* (2013.01); *C09K 11/06* (2013.01); *H01L 51/0058* (2013.01); *H01L 51/0072* (2013.01); *H05B 33/14* (2013.01); *C07C 2103/24* (2013.01); *C07C 2103/48* (2013.01); *C07C 2103/50* (2013.01); *C07C 2103/90* (2013.01); *C09K 2211/1007* (2013.01); *C09K 2211/1011* (2013.01); *C09K 2211/1029* (2013.01); *H01L 51/0054* (2013.01); *H01L 51/5012* (2013.01)

(58) Field of Classification Search
None
See application file for complete search history.

(56) References Cited

PUBLICATIONS

Pei et al., Selective Oxidative Cyclization by FeCl3 in the Construction of 10H-Indeno[1,2-b]triphenylene Skeletons in Polycyclic Aromatic Hydrocarbons, 2006, J. Org. Chem., vol. 71, pp. 6822-6828.*

*Primary Examiner* — Gregory Clark

(57) ABSTRACT

The present invention discloses a new indenotriphenylene derivatives and an organic light emitting device using the derivative. The organic light emitting device employing the new indenotriphenylene derivative as host material can lower driving voltage, prolong half-lifetime, increasing efficiency. The new indenotriphenylene derivative is represented by the following formula(A):

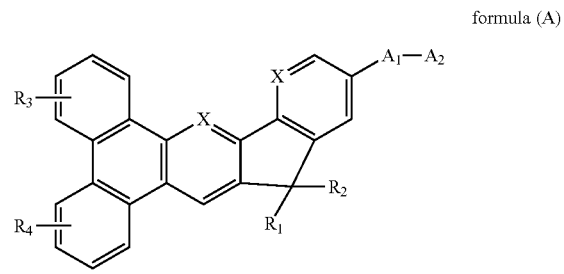

formula (A)

According to formula(A), $A_1$, $A_2$ are substituted or unsubstituted aromatic ring systems with one to five rings and independently selected from the group consisting of a phenyl group, a naphthyl group, an anthracenyl group, a pyrenyl group, a chrysenyl group and a perylenyl group. $R_1$ to $R_4$ are identical or different. $R_1$ to $R_4$ are independently selected from the group consisting of a hydrogen atom, a halide, an alkyl group having 1 to 20 carbon atoms, a substituted or unsubstituted aryl group having 6 to 30 carbon atoms, a substituted or unsubstituted aralkyl group having 6 to 30 carbon atoms and a substituted or unsubstituted heteroaryl group having 6 to 30 carbon atoms. X is selected from carbon atom or nitrogen atom.

10 Claims, 1 Drawing Sheet

(51) Int. Cl.
*C07D 221/18* (2006.01)
*C07D 471/04* (2006.01)
*C09K 11/06* (2006.01)
*H05B 33/14* (2006.01)
*H01L 51/00* (2006.01)

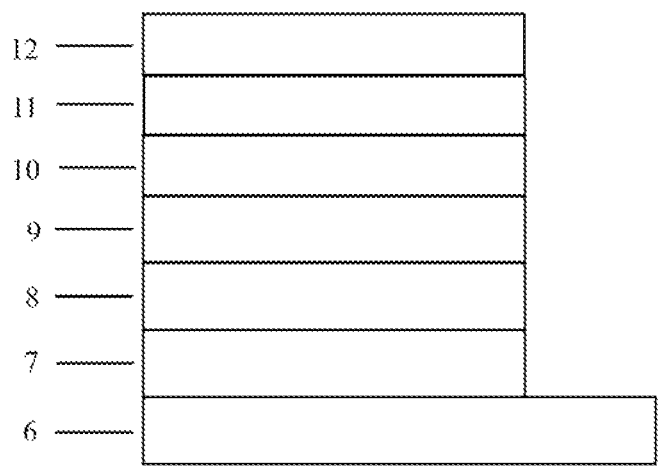

INDENOTRIPHENYLENE DERIVATIVES AND ORGANIC LIGHT EMITTING DEVICE USING THE SAME

FIELD OF INVENTION

The present invention generally relates to indenotriphenylene derivatives and organic light emitting device using the derivatives. More specifically, the present invention relates to indenotriphenylene derivatives having general formula(A), an organic light emitting device employing indenotriphenylene derivatives as emissive layer material can lower driving voltage, prolong half-lifetime, increasing efficiency and increasing the stability of organic light emitting device.

BACKGROUND OF THE INVENTION

Organic light-emitting devices (OLEDs) have received much attention due to their potential applications to full-colored flat panel displays. Especially small size AMOLED panels had been installed in smart phone these years. Larger size AMOLED panels also had been installed in TV for prototype DEMO. OLEDs are generally composed of functionally divided organic multi-layers, e.g., hole injection layer (HIL), hole transporting layer (HTL), emissive layer (EML), electron transporting layer (ETL) and electron injection layer (EIL) and so on. A emissive material have good charge carrier mobility and excellent operational durability can lower driving voltage and power consumption, increasing efficiency and half-lifetime of OLED.

For full-colored flat panel displays in AMOLED, the compounds used for the blue emissive layer are still unsatisfactory in half-lifetime and emissive colour. Many condensed aromatic compounds are used for blue host in emissive layer. U.S. Pat. No. 5,935,721 used 9,10-di(naphtha-2-yl)anthrance (AND) as blue host in emissive layer. U.S. Pat. No. 7,691,492 used 1,1'-(9,9-dimethyl-9H-fluorine-2,7-diyl)dipyrene (DFDP) as host for blue emitting electroluminescence device. U.S. Pat. No. 7,985,491 B2, U.S. Pat. No. 7,839,074 B2 claimed anthracene derivatives as host for blue organic electroluminescence device. These compounds still have disadvantages for industrial practice use. Especially for AMOLED, except prolong half-lifetime, deep blue emission (CIE y coordinates under 0.15) is necessary for improvement.

SUMMARY OF THE INVENTION

In accordance with the present invention, indenotriphenylene derivatives and their use for emissive material for OLEDs are provided. These indenotriphenylene derivatives can overcome the drawbacks of the conventional materials like as shorter half-life time, lower efficiency and CIE colour purity, especially for blue fluorescent emissive material in the present invention. For full-colored flat panel displays, the blue emissive material is still not satisfied for practice use for its shorter life and CIE colour purity. In order to obtain better thermal stability and practical operation durability, in the present invention, we introduce two repeated ring hydrocarbon units and link to a indenotriphenylene core to produce a novel indenotriphenylene derivatives. Triphenylene skeleton based derivative disclosed in U.S. Pat. No. 2004/0076853, WO2006/130598, WO2012035962A1, are used for organic EL device are described. There are no prior arts demonstrate an indenotriphenylene skeleton like the present invention formula(A) and used as fluorescent blue host for OLEDs.

An object of the present invention is to provide a novel class indenotriphenylene derivatives which can be used as emissive material for OLEDs.

Another object of the present invention is to apply these indenotriphenylene derivatives for blue emissive material of OLEDs and improve CIE colour purity & Dominate Wavelength.

Another object of the present invention is to apply these indenotriphenylene derivatives for blue emissive material of OLEDs and improve the half-lifetime, lower driving voltage, lower power consumption and increase the efficiency.

The present invention has the economic advantages for industrial practice. Accordingly, the present invention discloses indenotriphenylene derivatives which can be used for OLEDs is disclosed. The mentioned indenotriphenylene derivatives are represented by the following formula(A):

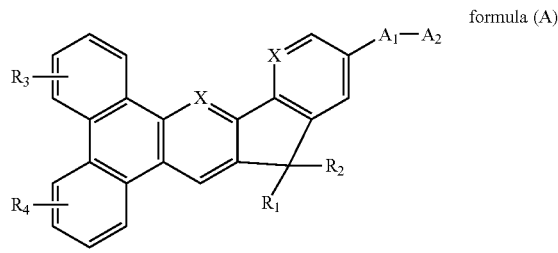

formula (A)

according to the formula(A), $A_1$, $A_2$ are substituted or unsubstituted aromatic ring systems with one to five rings and independently selected from the group consisting of a phenyl group, a naphthyl group, an anthracenyl group, a pyrenyl group, a chrysenyl group and a perylenyl group. $R_1$ to $R_4$ are identical or different. $R_1$ to $R_4$ are independently selected from the group consisting of a hydrogen atom, a halide, an alkyl group having 1 to 20 carbon atoms, a substituted or unsubstituted aryl group having 6 to 30 carbon atoms, a substituted or unsubstituted aralkyl group having 6 to 30 carbon atoms and a substituted or unsubstituted heteroaryl group having 6 to 30 carbon atoms. X is selected from carbon atom or nitrogen atom.

BRIEF DESCRIPTION OF THE DRAWINGS

FIG. 1 show one example of organic light emitting device in the present invention. 6 is transparent electrode, 12 is metal electrode, 7 is hole injection layer which is deposited onto 6, 8 is hole transporting layer which is deposited onto 7, 9 is fluorescent emitting layer which is deposited onto 8, 10 is electron transporting layer which is deposited onto 9, 11 is electron injection layer which is deposited onto 10.

DESCRIPTION OF THE PREFERRED EMBODIMENTS

What probed into the invention is indenotriphenylene derivatives and organic light emitting device using the compound. Detailed descriptions of the production, structure and elements will be provided in the following to make the invention thoroughly understood. Obviously, the application of the invention is not confined to specific details familiar to those who are skilled in the art. On the other hand, the common elements and procedures that are known to everyone are not described in details to avoid unnecessary limits of the invention. Some preferred embodiments of the present invention will now be described in greater detail in the following. However, it should be recognized that the present invention can be practiced in a wide range of other embodiments besides those explicitly described, that is, this invention can also be applied extensively to other embodiments, and the scope of the present invention is expressly not limited except as specified in the accompanying claims.

Definition

In a first embodiment of the present invention, indenotriphenylene derivatives which can be used as emissive material of OLEDs are disclosed. The mentioned indenotriphenylene derivatives are represented by the following formula(A):

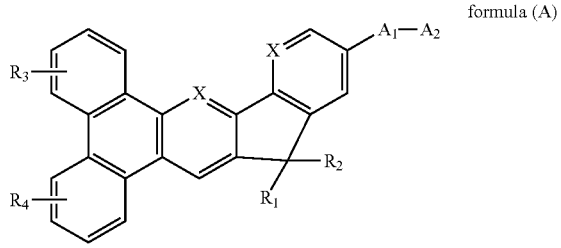

formula (A)

according to the formula(A), $A_1$, $A_2$ are substituted or unsubstituted aromatic ring systems with one to five rings and independently selected from the group consisting of a phenyl group, a naphthyl group, an anthracenyl group, a pyrenyl group, a chrysenyl group and a perylenyl group. R1 to R4 are identical or different. R1 to R4 are independently selected from the group consisting of a hydrogen atom, a halide, an alkyl group having 1 to 20 carbon atoms, a substituted or unsubstituted aryl group having 6 to 30 carbon atoms, a substituted or unsubstituted aralkyl group having 6 to 30 carbon atoms and a substituted or unsubstituted heteroaryl group having 6 to 30 carbon atoms. X is selected from carbon atom or nitrogen atom.

In this embodiment, some indenotriphenylene derivatives are shown below:

A1

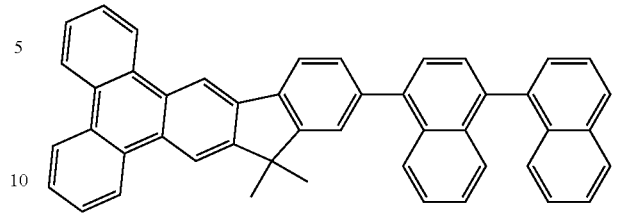

A2

A3

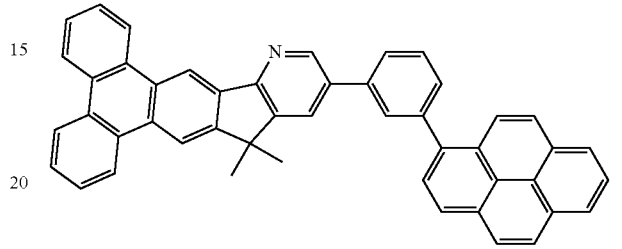

A4

A5

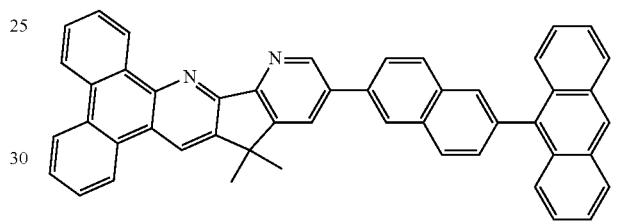

A6

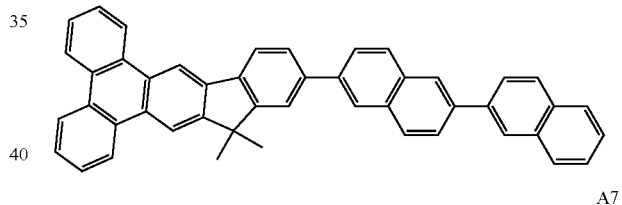

A7

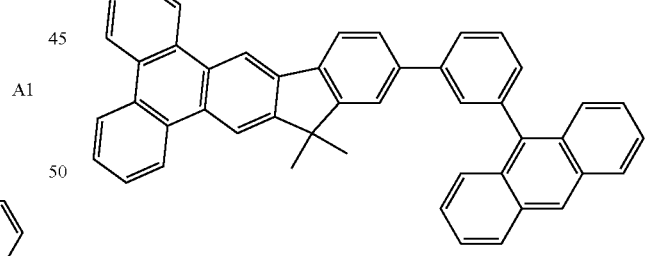

A8

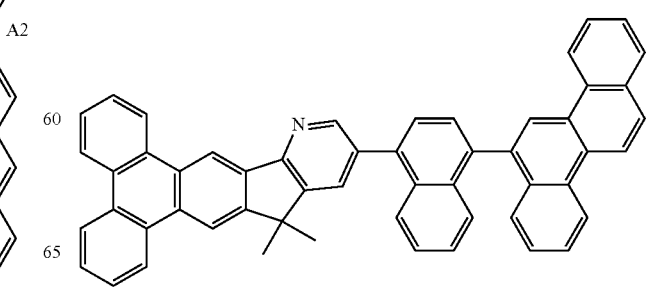

A9
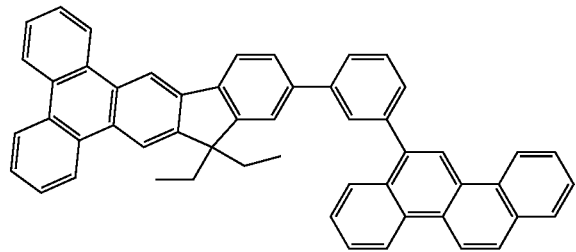
A10
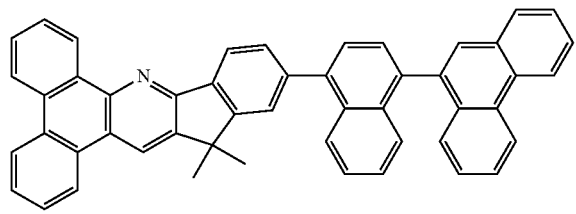
A11
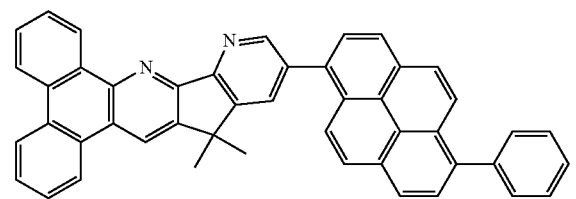
A12
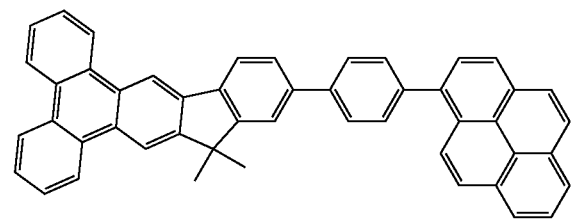
A13
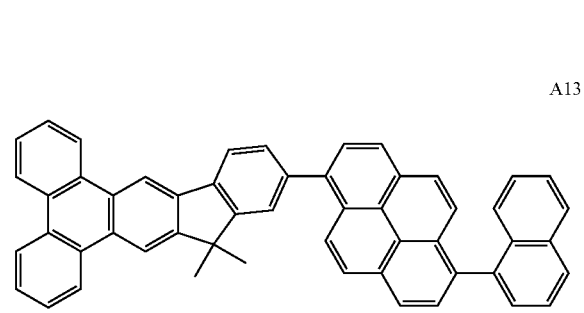
A14
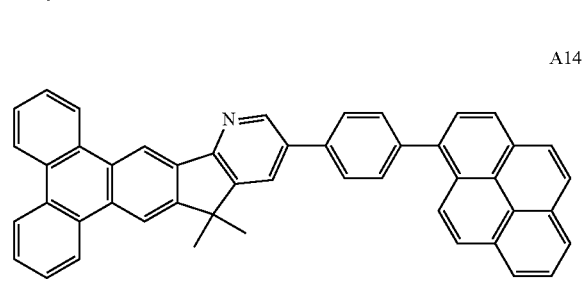
A15
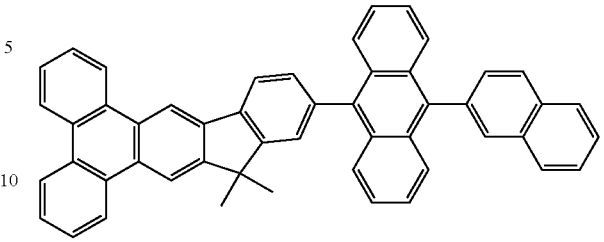
A16
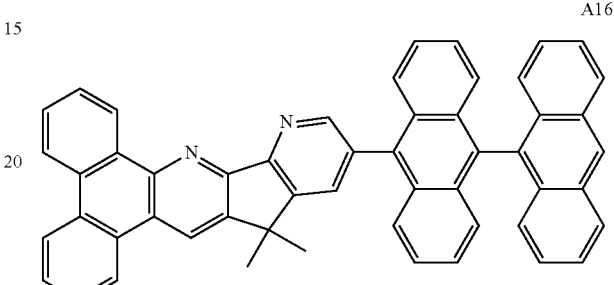
A17
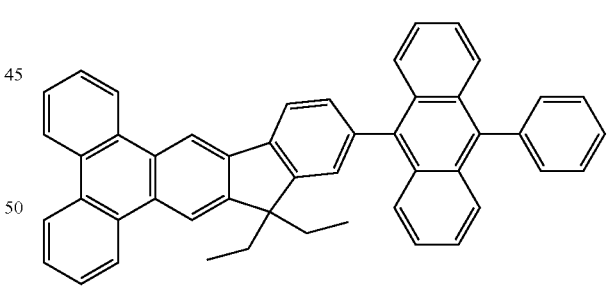
A18
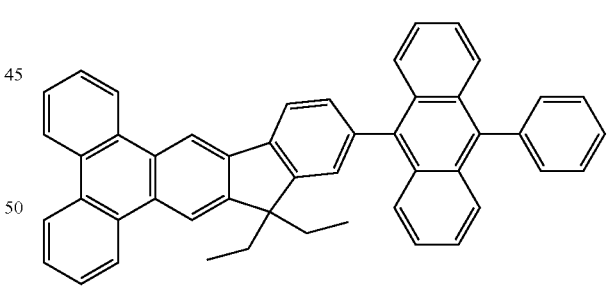
A19
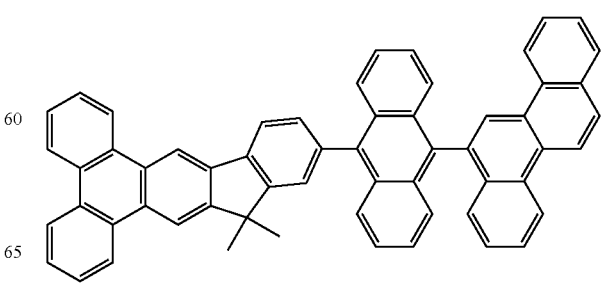

A20
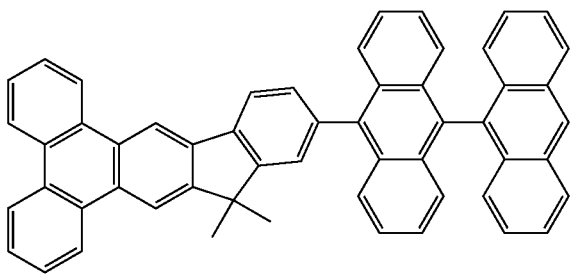
A21
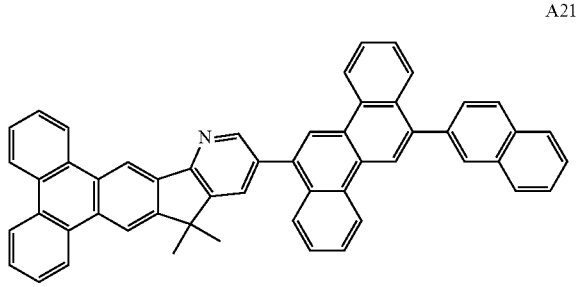
A22
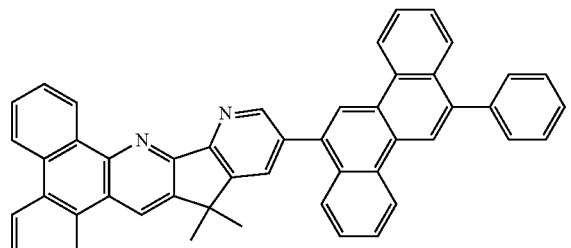
A23
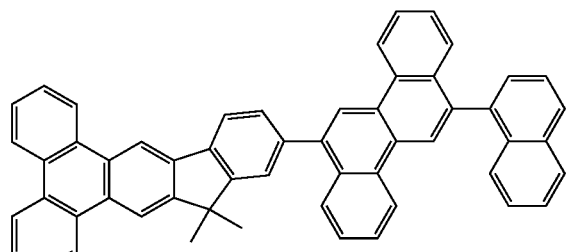
A24
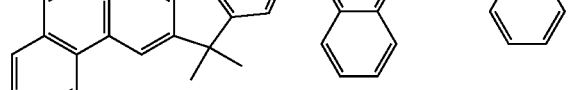
A25
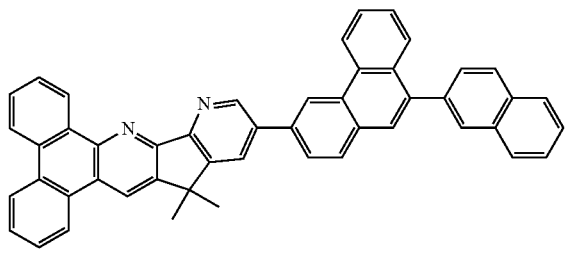
A26
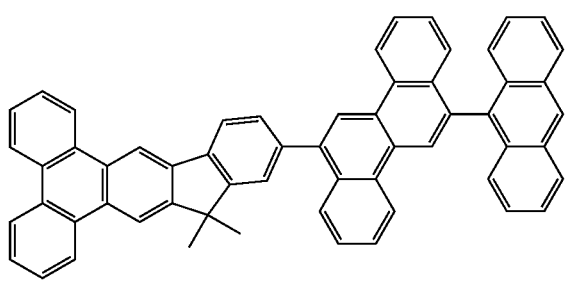
A27
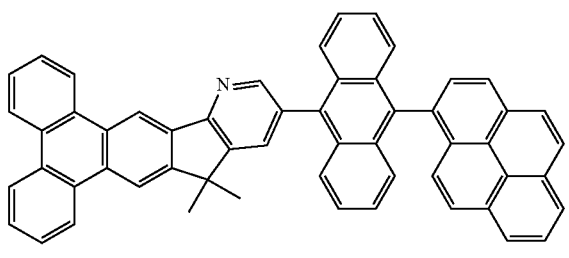
A28
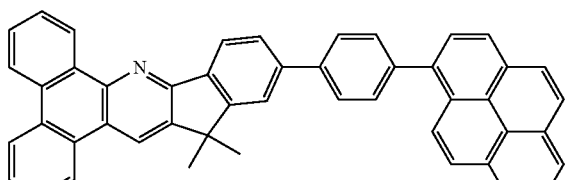
A29
A30
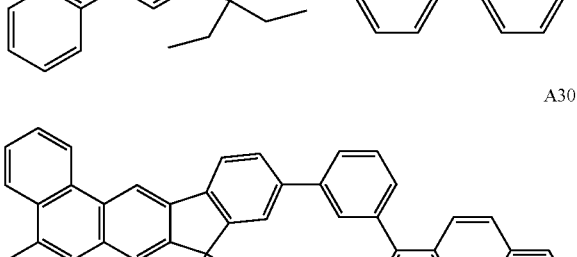

A31

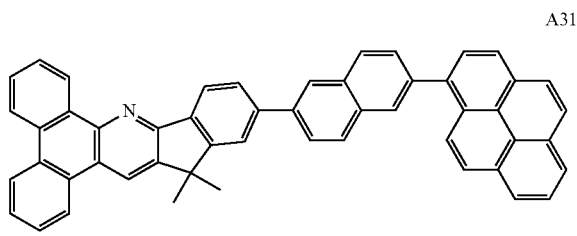

Indenotriphenylene derivatives for formula(A) can be prepared starting with dioxaborolane substituted Indenotriphenylene units Suzuki coupling with bromide substituted same or different aromatic ring systems with one to five rings like as Scheme I:

Scheme I

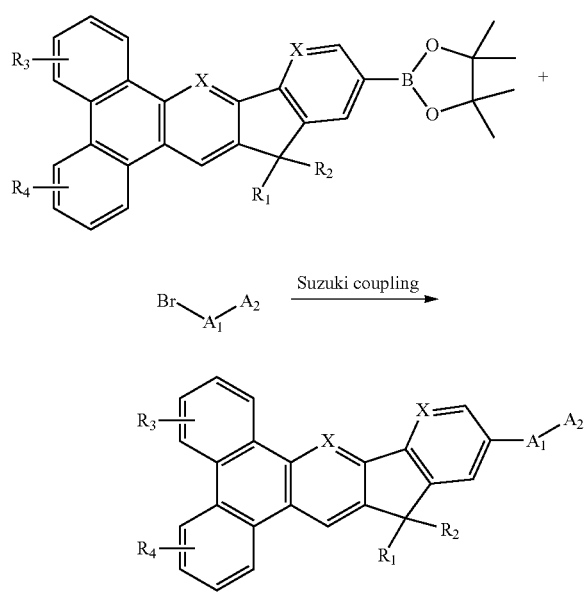

according to the formula(A), $A_1$, $A_2$ are substituted or unsubstituted aromatic ring systems with one to five rings and independently selected from the group consisting of a phenyl group, a naphthyl group, an anthracenyl group, a pyrenyl group, a chrysenyl group and a perylenyl group. $R_1$ to $R_4$ are identical or different. $R_1$ to $R_4$ are independently selected from the group consisting of a hydrogen atom, a halide, an alkyl group having 1 to 20 carbon atoms, a substituted or unsubstituted aryl group having 6 to 30 carbon atoms, a substituted or unsubstituted aralkyl group having 6 to 30 carbon atoms and a substituted or unsubstituted heteroaryl group having 6 to 30 carbon atoms. X is selected from carbon atom or nitrogen atom.

Dioxaborolane substituted Indenotriphenylene units can be prepared starting with biphenyl-2-ylboronic acid Suzuki coupling with dibromo substituted units (Intermediate Ia) to get the desire Intermediate Ib, then proceed FeCl₃ oxidative coupling reaction into the substituted Indenotriphenylene units and finally convert into desire Dioxaborolane substituted Indenotriphenylene units like as Scheme II:

Scheme II

[Scheme II reaction showing biphenyl-2-ylboronic acid + dibromo intermediate → Intermediate Ia → Intermediate Ib with reagents Pd(PPh₃)₄, Na₂CO₃, Toluene/Ethanol; then FeCl₃; then bis(pinacolato)diboron, Pd(PPh₃)₄, KOAc]

Br-$A_1$-$A_2$ can be prepared like as Scheme III

Scheme III

Br—$A_1$—Br + $A_2$—B(OH)₂ $\xrightarrow{\text{Pd(PPh}_3\text{)}_4,\ \text{Na}_2\text{CO}_3}{\text{Toluene/Ethanol}}$ Br—$A_1$—$A_2$ Important $(Br)_2A_1$ structure can be represented as following:

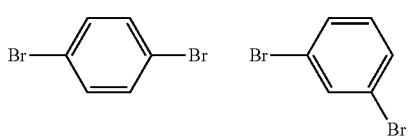

-continued

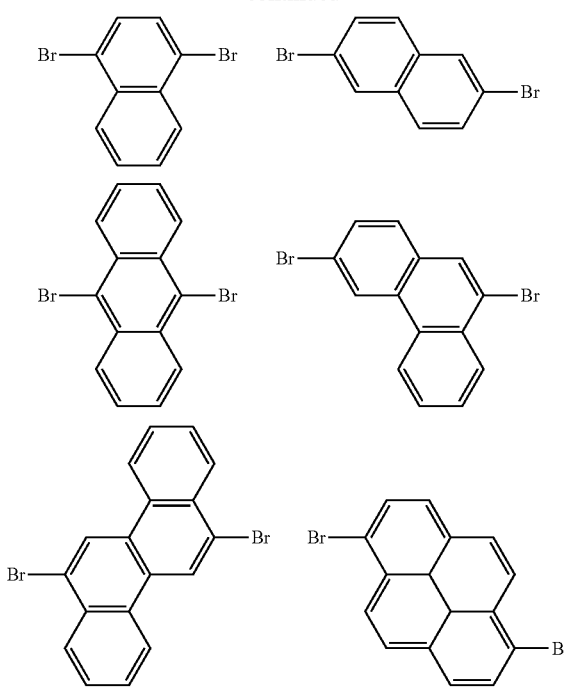

Important A$_2$—B(OH)$_2$ structure can be represented as following:

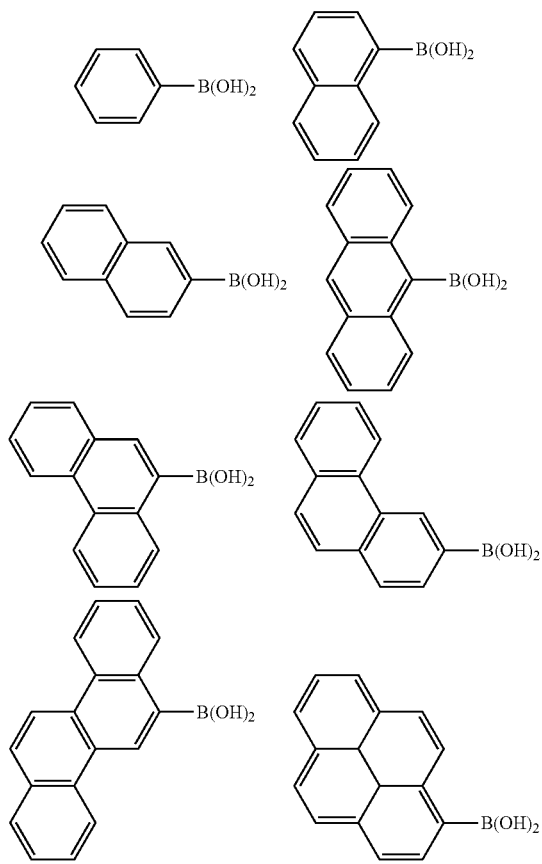

Detailed preparation for formula(A) could be clarified by exemplary embodiments, but the present invention is not limited to exemplary embodiments.

EXAMPLE 1

Synthesis of Compound A12

Synthesis of 2-(biphenyl-2-yl)-7-bromo-9,9-dimethyl-9H-fluorene

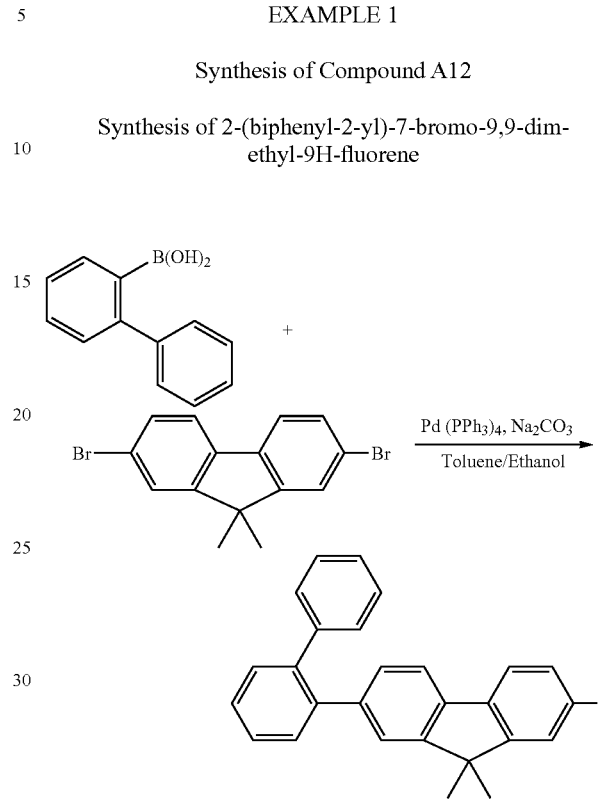

A mixture of 35.2 g (100 mmol) of 2,7-dibromo-9,9-dimethyl-9H-fluorene, 21.8 g (110 mmol) of biphenyl-2-ylboronic acid, 2.31 g (2 mmol) of Tetrakis(triphenylphosphine) Palladium, 75 ml of 2M Na$_2$CO$_3$, 150 ml of EtOH and 300 ml toluene was degassed and placed under nitrogen, and then heated at 100° C. for 12 h. After the reaction finish, the mixture was allowed to cool to room temperature. The organic layer was extracted with ethyl acetate and water, dried with anhydrous magnesium sulfate, the solvent was removed and the residue was purified by column chromatography on silica (hexane-dichloromethane) to give product (26.8 g, 63.0 mmol, 63%) as a white solid. $^1$H NMR (CDCl$_3$, 400 MHz): chemical shift(ppm) 7.61 (d, J=7.8 Hz, 1H), 7.55~7.53 (m, 2H), 7.49~7.42 (m, 5H), 7.29 (d, J=8.0 Hz, 1H), 7.20~7.14 (m, 5H), 6.98 (s, 1H), 1.21 (s, 6H)

Synthesis of 12-bromo-10,10-dimethyl-10H-indeno[1,2-b]triphenylene

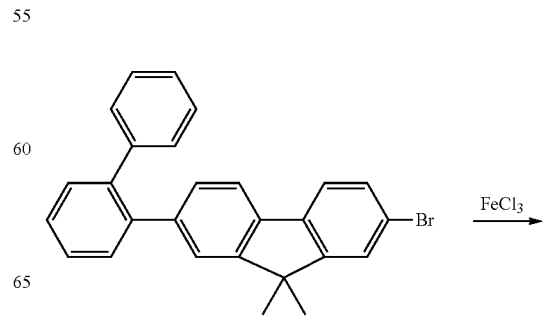

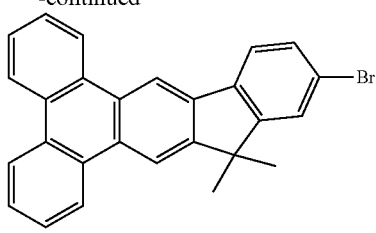

In a 3000 ml three-necked flask that had been degassed and filled with nitrogen, 26.8 g (63 mmol) of 2-(biphenyl-2-yl)-7-bromo-9,9-dimethyl-9H-fluorene was dissolved in anhydrous Dichloromethane (1500 ml), 102.4 g (630 mmol) iron (III) chloride was then added, and the mixture was stirred one hour. Methanol 500 ml were added to the mixture and the organic layer was separated and the solvent removed in vacuo. The residue was purified by column chromatography on silica (hexane-dichloromethane) afforded a white solid (10.7 g, 25.3 mmol, 40%). $^1$H NMR (CDCl$_3$, 400 MHz): chemical shift(ppm) 8.95 (s, 1H), 8.79~8.74 (m, 2H), 8.69~8.68 (m, 3H), 7.84 (d, J=8.0 Hz, 1H), 7.72~7.65 (m, 5H), 7.57 (d, J=8.0 Hz, 1H), 1.66 (s, 6H).

Synthesis of 2-(10,10-dimethyl-10H-indeno[1,2-b]triphenylen-12-yl)-4,4,5,5-tetramethyl-1,3,2-dioxaborolane

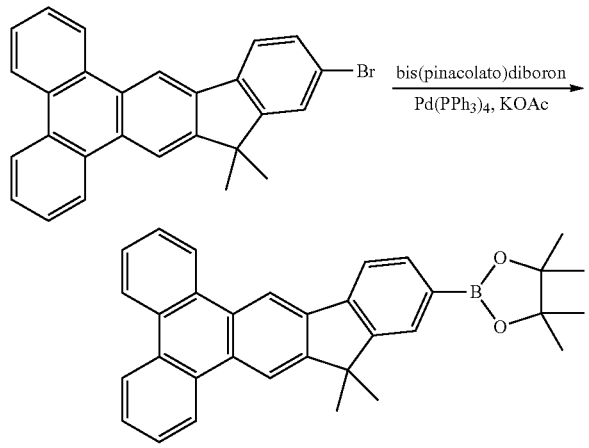

A mixture of 10.7 g (25.3 mmol) of 12-bromo-10,10-dimethyl-10H-Indeno[1,2-b]triphenylene, 7.7 g (30.3 mmol) of bis(pinacolato) diboron, 0.3 g (0.26 mmol) of Tetrakis(triphenylphosphine)Palladium, 7.4 g (75.4 mmol) of potassium acetate, and 300 ml 1,4 dioxane was degassed and placed under nitrogen, and then heated at 90° C. for 16 h. After the reaction finish, the mixture was allowed to cool to room temperature. The organic phase separated and washed with ethyl acetate and water. After drying over magnesium sulfate, the solvent was removed in vacuo. The residue was purified by column chromatography on silica (hexane-dichloromethane) to give product (9.5 g, 20.2 mmol, 80%) as a light-yellow solid. $^1$H NMR (CDCl$_3$, 400 MHz): chemical shift(ppm) 9.03 (s, 1H), 8.81 (d, J=7.84 Hz, 1H), 8.77 (d, J=7.88 Hz, 1H), 8.70~8.67 (m, 3H), 8.02~7.93 (m, 3H), 7.71~7.67 (m, 4H), 1.69 (s, 6H), 1.42 (s, 12H)

Synthesis of Pyren-1-ylboronic acid

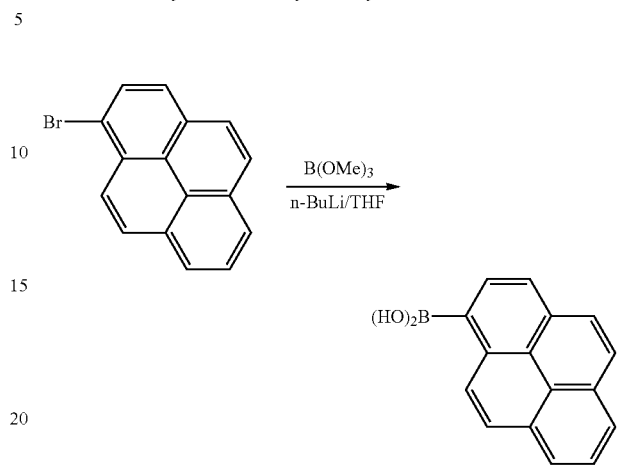

An excess of 1.6 M n-BuLi in hexane (50 mL, 80 mmol) was added to a solution of 1-bromopyrene (20.4 g, 72.6 mmol) in 500 ml dry tetrahydrofuran at −78° C. under N$_2$. The reaction mixture was then maintained at 0° C. for 1 h before cooling to −78° C. Trimethyl borate (10.4 g, 100 mmol) was added dropwise; the solution was then warmed slowly to room temperature and stirred for 24 h. 2N HCl (150 ml) was added and then the mixture was stirred for a further 1 h. The reaction mixture was extracted with ethyl acetate and water, dried with anhydrous magnesium sulfate, the solvent was evaporated in vacuo, and the residue was crystallized (n-hexane) to give the pyren-1-ylboronic acid 12.5 g as a yellow solid (70%)

Synthesis of 1-(4-bromophenyl)pyrene

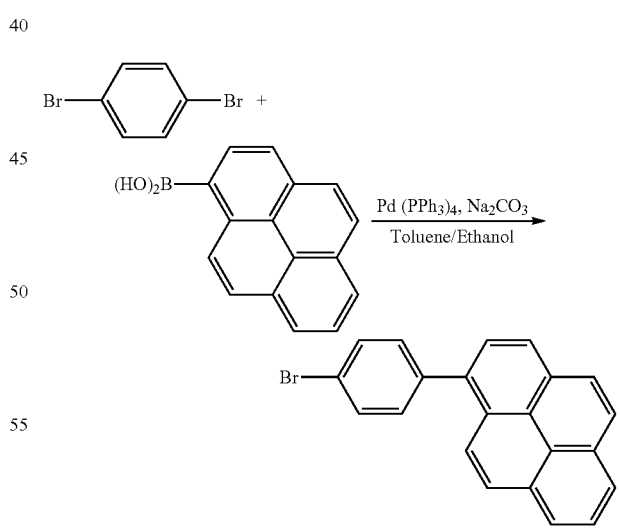

A mixture of 10 g (42.4 mmol) 1,4-dibromobenzene, 10.43 g (42.4 mmol) of Pyren-1-ylboronic acid, 0.5 g (0.424 mmol) of Tetrakis(triphenylphosphine)Palladium, 32 ml of 2M Na$_2$CO$_3$, 80 ml of EtOH and 160 ml toluene was degassed and placed under nitrogen, and then heated at 90° C. for 24 h. After the reaction finish, the mixture was allowed to cool to room temperature. The organic layer was extracted with ethyl acetate and water, dried with anhydrous magnesium sulfate, the solvent was removed and the residue was purified by column chromatography on silica (hexane-dichloromethane) to give product 9.5 g (63%) as a white solid.

Synthesis of 10,10-dimethyl-12-(4-(pyren-1-yl)phenyl)-10H-indeno[1,2-b]triphenylene

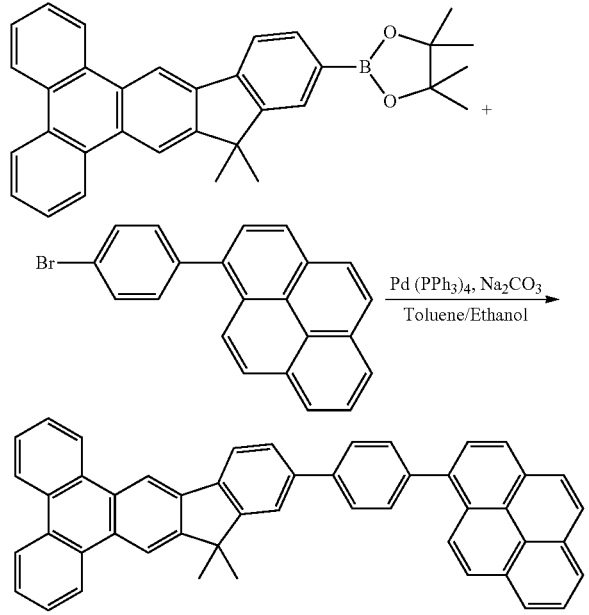

A mixture of 5 g (14 mmol) of 1-(4-bromophenyl)pyrene, of 7.53 (16 mmol) 2-(10,10-dimethyl-10H-indeno[1,2-b]triphenylen-12-yl)-4,4,5,5-tetramethyl-1,3,2-dioxaborolane, 0.16 g (0.14 mmol) of Tetrakis(triphenylphosphine)palladium, 11 ml of 2M $Na_2CO_3$, 30 ml of EtOH and 65 ml toluene was degassed and placed under nitrogen, and then heated at 90° C. for 12 h. After the reaction finish, the mixture was allowed to cool to room temperature. Than 500 ml MeOH was added, while stirring and the precipitated product was filtered off with suction. To give 4.95 g (yield 57%) of yellow product which was recrystallized from toluene. MS(m/z,FAB$^+$): 620.2; $^1$H NMR (CDCl$_3$, 400 MHz): chemical shift(ppm) 9.06 (s, 1H), 8.86 (d, J=8.00 Hz, 1H), 8.80 (d, J=8.00 Hz, 1H), 8.75 (s, 1H), 8.71 (d, J=8.00 Hz, 2H), 8.33~8.27 (m, 2H), 8.22~8.20 (m, 2H), 8.14~8.05 (m, 6H), 7.94 (d, J=8.00 Hz, 2H), 7.89 (s, 1H), 7.85~7.69 (m, 7H), 1.77 (s, 6H).

EXAMPLE 2

Synthesis of Compound A13

Synthesis of 1-bromo-6-(naphthalen-1-yl)pyrene

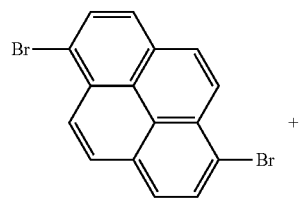

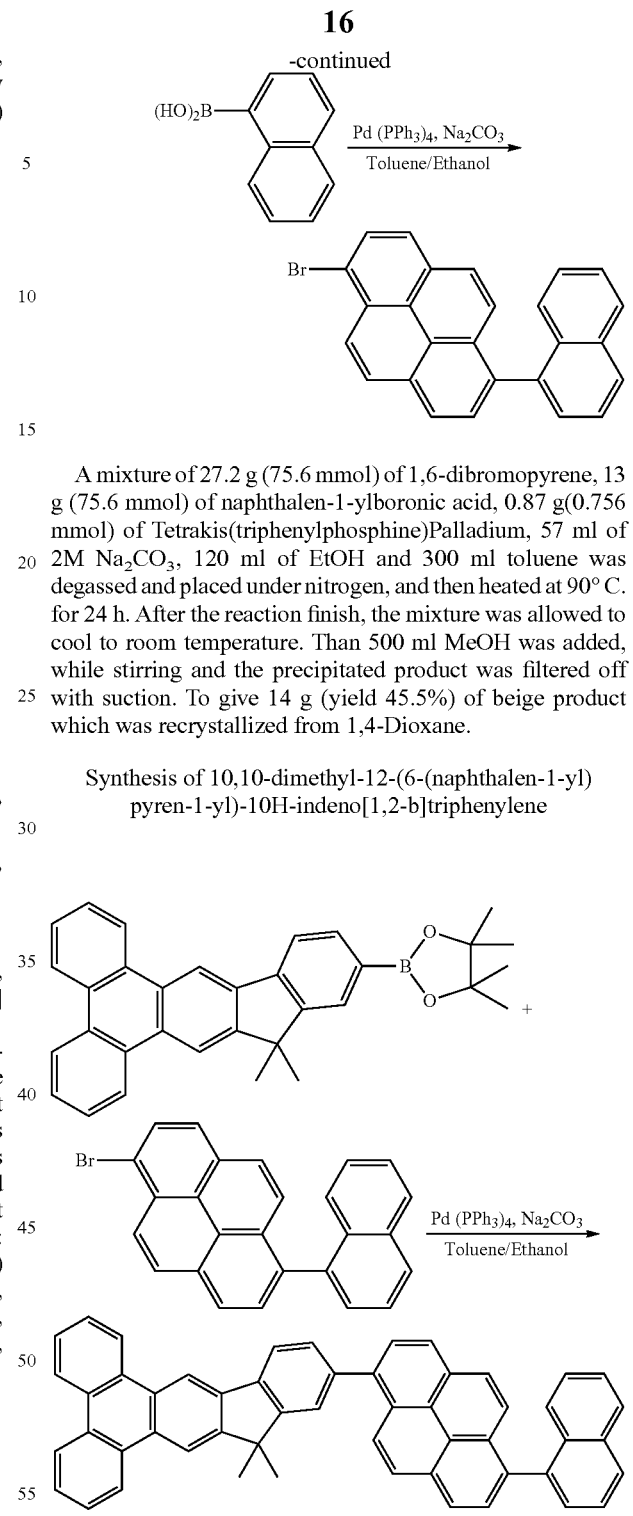

A mixture of 27.2 g (75.6 mmol) of 1,6-dibromopyrene, 13 g (75.6 mmol) of naphthalen-1-ylboronic acid, 0.87 g (0.756 mmol) of Tetrakis(triphenylphosphine)Palladium, 57 ml of 2M $Na_2CO_3$, 120 ml of EtOH and 300 ml toluene was degassed and placed under nitrogen, and then heated at 90° C. for 24 h. After the reaction finish, the mixture was allowed to cool to room temperature. Than 500 ml MeOH was added, while stirring and the precipitated product was filtered off with suction. To give 14 g (yield 45.5%) of beige product which was recrystallized from 1,4-Dioxane.

Synthesis of 10,10-dimethyl-12-(6-(naphthalen-1-yl)pyren-1-yl)-10H-indeno[1,2-b]triphenylene A mixture of 7 g (17.2 mmol) of 1-bromo-6-(naphthalen-1-yl)pyrene, 8.1 g (17.2 mmol) of 2-(10,10-dimethyl-10H-indeno[1,2-b]triphenylen-12-yl)-4,4,5,5-tetramethyl-1,3,2-dioxaborolane, 0.2 g (0.172 mmol) of Tetrakis(triphenylphosphine)Palladium, 13 ml of 2M $Na_2CO_3$, 30 ml of EtOH and 100 ml toluene was degassed and placed under nitrogen, and then heated at 90° C. for 24 h. After the reaction finish, the mixture was allowed to cool to room temperature. Than 500 ml MeOH was added, while stirring and the precipitated product was filtered off with suction. To give 5.4 g (yield 47%) of yellow product which was recrystallized from toluene. MS(m/z,FAB+): 670.1; $^1$H NMR (CDCl$_3$, 400 MHz): chemical shift(ppm) 9.11 (s, 1H), 8.89 (d, J=8.00 Hz, 1H), 8.82 (d, J=8.00 Hz, 1H), 8.78 (s, 1H), 8.72 (d, J=8.00 Hz, 2H), 8.38 (d, J=9.20 Hz, 1H), 8.30~8.26 (m, 3H), 8.19~8.05 (m, 7H), 8.02~7.98 (m, 2H), 7.83~7.82 (m, 2H), 7.78~7.68 (m, 5H), 7.61~7.59 (m, 2H), 1.79 (s, 6H).

EXAMPLE 3

Synthesis of Compound A15

Synthesis of 9-bromo-10-(naphthalen-2-yl)anthracene

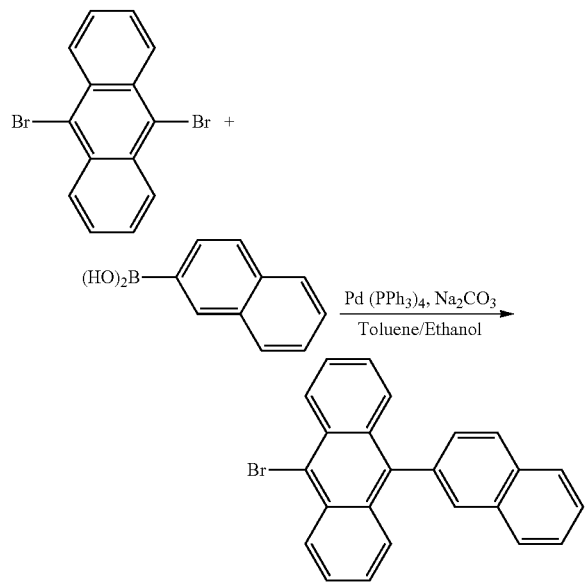

A mixture of 15 g (44.6 mmol) of 9,10-dibromoanthracene, 7.7 g (44.6 mmol) of naphthalen-2-ylboronic acid, 0.52 g (0.446 mmol) of Tetrakis(triphenylphosphine)Palladium, 33 ml of 2M Na$_2$CO$_3$, 60 ml of EtOH and 150 ml toluene was degassed and placed under nitrogen, and then heated at 90° C. for 24 h. After the reaction finish, the mixture was allowed to cool to room temperature. The organic layer was extracted with ethyl acetate and water, dried with anhydrous magnesium sulfate, the solvent was removed and the residue was purified by column chromatography on silica (hexane-dichloromethane) to give product 10.4 g (61%) as a yellow solid.

Synthesis of 10,10-dimethyl-12-(10-(naphthalen-2-yl)anthracen-9-yl)-10H-indeno[1,2-b]triphenylene

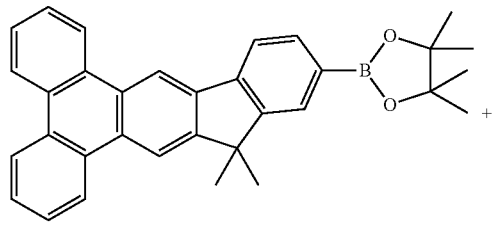

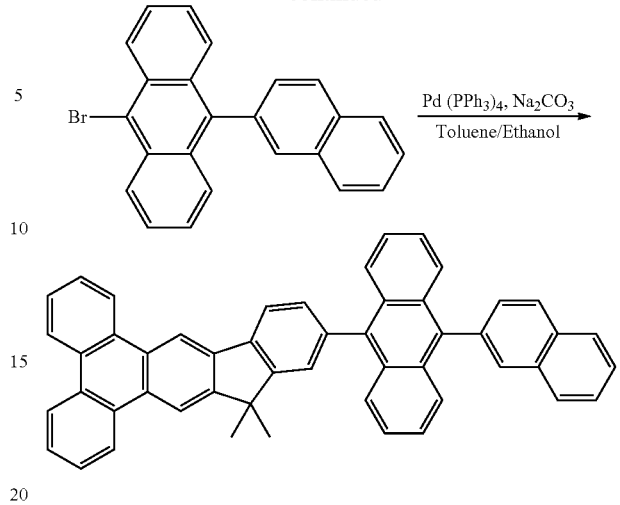

A mixture of 6.6 g (17.2 mmol) of 9-bromo-10-(naphthalene-2-yl)anthracene, 8.1 g (17.2 mmol) of 2-(10,10-dimethyl-10H-indeno[1,2-b]triphenylen-12-yl)-4,4,5,5-tetramethyl-1,3,2-dioxaborolane, 0.2 g (0.172 mmol) of Tetrakis(triphenylphosphine)palladium, 13 ml of 2M Na$_2$CO$_3$, 30 ml of EtOH and 100 ml toluene was degassed and placed under nitrogen, and then heated at 90° C. for 24 h. After the reaction finish, the mixture was allowed to cool to room temperature. Than 500 ml MeOH was added, while stirring and the precipitated product was filtered off with suction. To give 5.9 g (yield 53%) of yellow product which was recrystallized from toluene. MS(m/z,FAB+): 646.4; $^1$H NMR (CDCl$_3$, 400 MHz): chemical shift(ppm) 9.14 (s, 1H), 8.90 (d, J=7.80 Hz, 1H), 8.82 (d, J=7.92 Hz, 1H), 8.79 (s, 1H), 8.73 (d, J=7.88 Hz, 2H), 8.23 (d, J=7.72 Hz, 1H), 8.11 (d, J=8.24 Hz, 1H), 8.07~8.02 (m, 2H), 7.96 (d, J=7.40 Hz, 1H), 7.89 (d, J=8.64 Hz, 2H), 7.78~7.59 (m, 10H), 7.42~7.33 (m, 4H), 7.20 (d, J=7.40 Hz, 1H), 1.76 (s, 6H).

EXAMPLE 4

Synthesis of Compound A27

Synthesis of 5H-indeno[1,2-b]pyridin-5-one

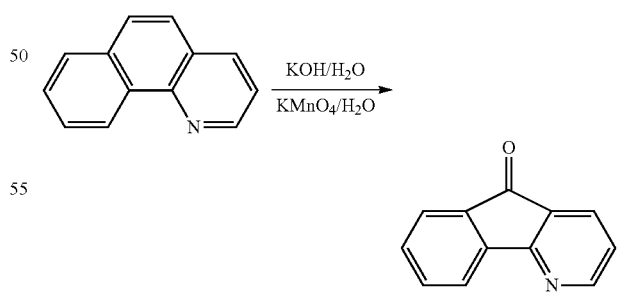

A solution of benzo[h]quinoline (6 g, 33.5 mmol) and KOH (5.6 g, 100.5 mmol) in water (400 mL) was boiled. A hot solution of KMnO$_4$ (14.8 g, 93.8 mmol) in water (240 mL) was added dropwise over 1 hour to the boiling solution. The mixture was refluxed for another 6 hours and filtered hot. The filtrate was allowed to cool to room temperature. The organic layer was extracted with chloroform and water, dried with anhydrous magnesium sulfate. After solvent removal, the residue was purified by column chromatography on silica (acetone-petroleum ether) to give product 2.5 g (42%) as a yellow solid.

Synthesis of 5H-indeno[1,2-b]pyridine

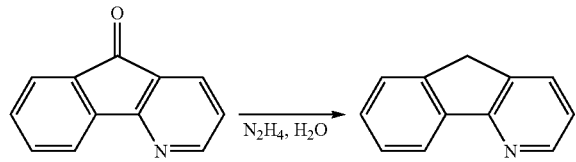 [SMILES: O=C1c2ccccc2-c2ncccc21 ; c1ccc2c(c1)Cc1cccnc1-2]

A mixture of 18.1 g (100 mmol) of 5H-indeno[1,2-b]pyridin-5-one, 27 ml (400 mmol) of hydrazine monohydrate, and 500 ml diethylene glycol was degassed and placed under nitrogen, and then heated at 170° C. for 12 h. After the reaction finish, the mixture was allowed to cool to room temperature. The organic layer was extracted with ethyl acetate and water, dried with anhydrous magnesium sulfate, the solvent was removed to give product 13.5 g (81%).

Synthesis of 5,5-dimethyl-5H-indeno[1,2-b]pyridine

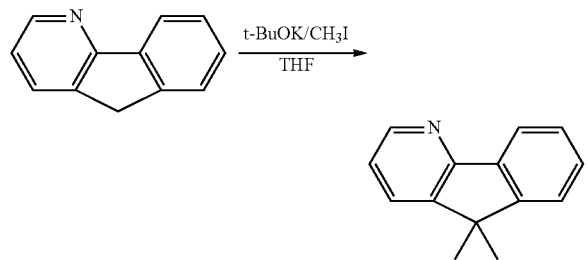

13.5 g (80.7 mmol) of 5H-indeno[1,2-b]pyridine was dissolved in 120 ml dry tetrahydrofuran, and 22.7 g (202 mmol) of potassium tert-butoxide was added to the solution at −10° C. The reaction mixture was maintained at −10° C. for 1 hour. Then the iodomethane 28.7 g (202 mmol) was added dropwise; the solution was then warmed slowly to room temperature and stirred for 6 h. After the reaction completion, water was added to the mixture to terminate the reaction. The reaction mixture was extracted with ethyl acetate and water, dried with anhydrous magnesium sulfate, the solvent was evaporated in vacuo, and the residue was crystallized with toluene to give the 5,5-dimethyl-5H-indeno[1,2-b]pyridine, 13.5 g (86%)

Synthesis of 3,7-dibromo-5,5-dimethyl-5H-indeno[1,2-b]pyridine

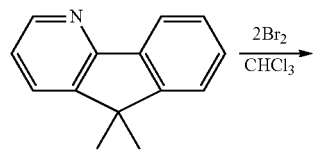

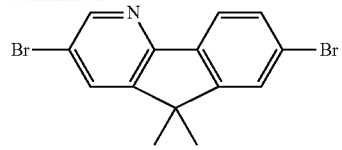

5,5-dimethyl-5H-indeno[1,2-b]pyridine (13.5 g, 69.1 mmol) was dissolved in chloroform (300 mL), protected from light and bromine (23.2 g, 145.1 mmol) diluted in chloroform (50 ml) was added dropwise. The mixture was stirred for 24 hours at room temperature, after which water (600 ml) was added, then the precipitated product was filtered off with suction, washed with MeOH and recrystallized from chloroform to give the 3,7-dibromo-5,5-dimethyl-5H-indeno[1,2-b]pyridine 13 g (53%)

Synthesis of Structural Isomerism with 7-(biphenyl-2-yl)-3-Bromo-5,5-dimethyl-5H-indeno[1,2-b]pyridine and 3-(biphenyl-2-yl)-7-bromo-5,5-dimethyl-5H-indeno[1,2-b]pyridine

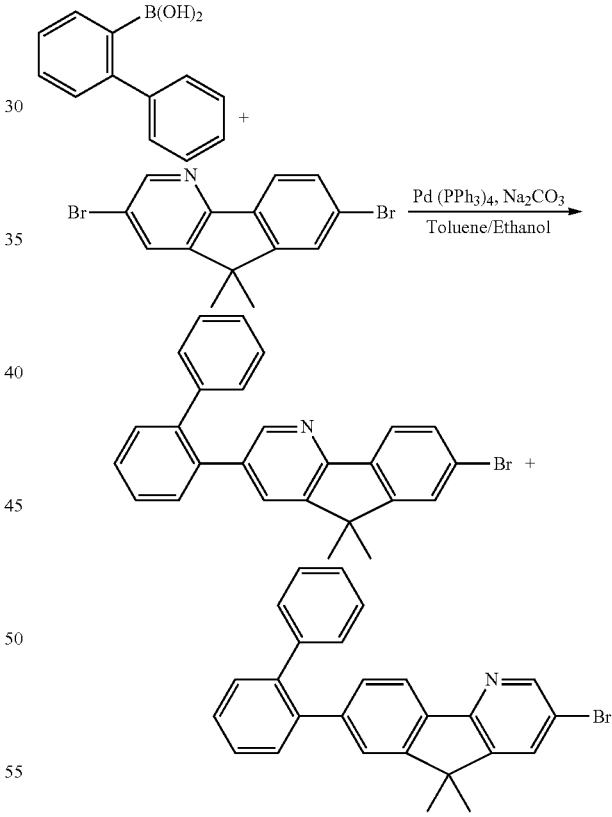

A mixture of 13 g (36.8 mmol) of 3,7-dibromo-5,5-dimethyl-5H-indeno[1,2-b]pyridine, 8.7 g (44 mmol) of biphenyl-2-ylboronic acid, 0.43 g (0.368 mmol) of Tetrakis(triphenylphosphine)Palladium, 28 ml of 2M $Na_2CO_3$, 50 ml of EtOH and 120 ml toluene was degassed and placed under nitrogen, and then heated at 90° C. for 24 h. After the reaction finish, the mixture was allowed to cool to room temperature. The organic layer was extracted with ethyl acetate and water, dried with anhydrous magnesium sulfate, the solvent was removed and the residue was washed with MeOH to give the structural isomerism product (10.4 g, 66%) which was used without further purification.

Synthesis of 12-bromo-10,10-dimethyl-10H-cyclopenta[b]pyridine[1,2-b]triphenylene and 12-bromo-10,10-dimethyl-10H-dibenzo[f,h]Indeno[1,2-b]quinoline

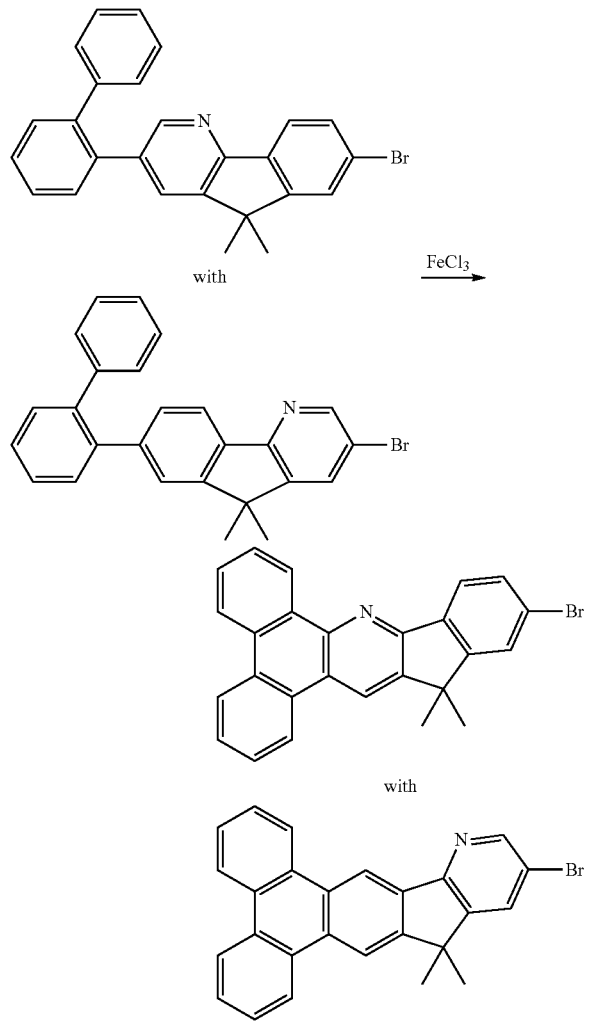

In a 2000 ml three-necked flask that had been degassed and filled with nitrogen, 10.4 g (24.4 mmol) of structural isomerism with 7-(biphenyl-2-yl)-3-bromo-5,5-dimethyl-5H-indeno[1,2-b]pyridine and 3-(biphenyl-2-yl)-7-bromo-5,5-dimethyl-5H-indeno[1,2-b]pyridine was dissolved in anhydrous dichloromethane (600 ml), 39.5 g (244 mmol) Iron(III) chloride was then added, and the mixture was stirred one hour. Methanol 500 ml were added to the mixture and the organic layer was separated and the solvent removed in vacuo. The residue was purified by column chromatography on silica (hexane-dichloromethane) to give 12-bromo-10,10-dimethyl-10H-cyclopenta[b]pyridino[1,2-b]triphenylene (1.8 g, 17.4%); $^1$H NMR (CDCl$_3$, 400 MHz): chemical shift (ppm) 9.08 (s, H), 8.76 (s, 1H), 8.46~8.41 (m, 2H), 8.38 (s, 1H), 8.05 (d, J=8.00 Hz, 1H), 7.96 (d, J=8.00 Hz, 1H), 7.74 (s, 1H), 7.66~7.49 (m, 4H), 1.73 (s, 6H). and 12-bromo-10,10-dimethyl-10H-dibenzo[f,h]indeno[1,2-b]quinoline (3.7 g, 35.7%).; $^1$H NMR (CDCl$_3$, 400 MHz): chemical shift(ppm) 8.62~8.52 (m, 3H), 8.31 (s, 1H), 8.02 (d, J=8.00 Hz, 1H), 7.66~7.57 (m, 3H), 7.30 (t, J=8.00 Hz, 1H), 7.22 (s, 1H), 7.14~7.00 (m, 2H), 1.79 (s, 6H).

Synthesis of 4,4,5,5-tetramethyl-1,3,2-dioxaborolane-10,10-dimethyl-10H-cyclopenta[b]pyridino[1,2-b]triphenylene

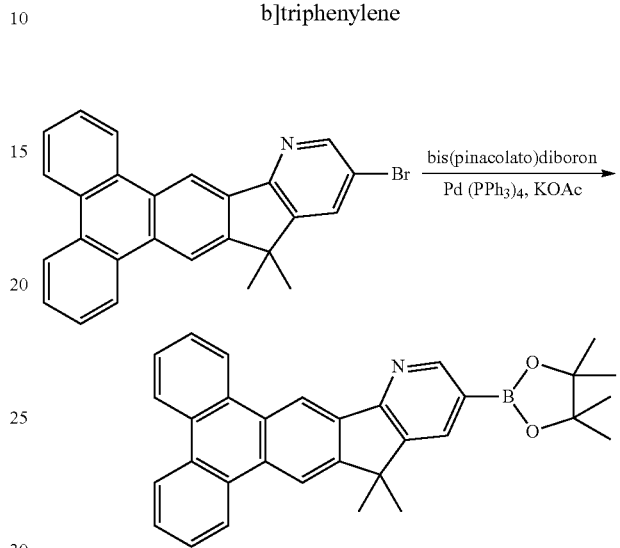

A mixture of 3 g (7 mmol) 12-bromo-10,10-dimethyl-10H-cyclopenta[b]pyridino[1,2-b]triphenylene, 2 g (7.9 mmol) of bis(pinacolato)diboron, 0.085 g (0.07 mmol) of Tetrakis(triphenylphospine)Palladium, 2 g (21 mmol) of potassium acetate, and 50 ml 1,4 dioxane was degassed and placed under nitrogen, and then heated at 90° C. for 8 h. After the reaction finish, the mixture was allowed to cool to room temperature. The organic phase separated and washed with ethyl acetate and water. After drying over magnesium sulfate, the solvent was removed in vacuo. The residue was purified by column chromatography on silica (hexane-dichloromethane) to give product (2.65 g, 80%) as a light-yellow solid.

Synthesis of 1-(10-bromoanthracen-9-yl)pyrene

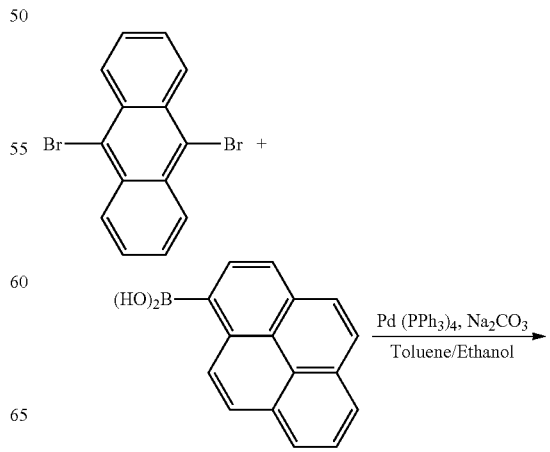

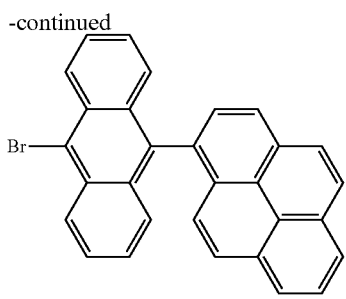

A mixture of 15 g (44.6 mmol) of 9,10-dibromoanthracene, 11 g (44.6 mmol) of pyren-1-ylboronic acid, 0.52 g (0.446 mmol) of Tetrakis(triphenylphosphine)palladium, 33 ml of 2M Na₂CO₃, 60 ml of EtOH and 150 ml toluene was degassed and placed under nitrogen, and then heated at 90° C. for 24 h. After the reaction finish, the mixture was allowed to cool to room temperature. The organic layer was extracted with ethyl acetate and water, dried with anhydrous magnesium sulfate, the solvent was removed and the residue was purified by column chromatography on silica (hexane-dichloromethane) to give product 8.8 g (43%) as a yellow solid.

Synthesis of Compound A27

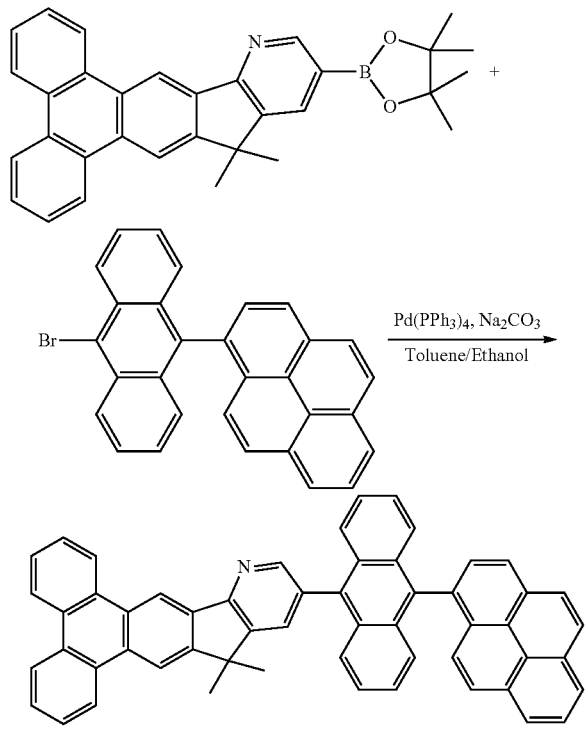

A mixture of 2.6 g (5.6 mmol) of 1-(10-bromoanthracen-9-yl)pyrene, 2.65 g (5.6 mmol) of 4,4,5,5-tetramethyl-1,3,2-dioxaborolane-10,10-dimethyl-10H-cyclopenta[b]pyridino[1,2-b]triphenylene, 0.06 g (0.056 mmol) of Tetrakis(triphenylphosphine)Palladium, 4.2 ml of 2M Na₂CO₃, 15 ml of EtOH and 50 ml toluene was degassed and placed under nitrogen, and then heated at 100° C. for 24 h. After the reaction finish, the mixture was allowed to cool to room temperature. Than 100 ml MeOH was added, while stirring and the precipitated product was filtered off with suction. To give 2.1 g (yield 53%) of yellow product which was recrystallized from toluene. MS(m/z;FAB⁺): 721.1; ¹H NMR (CDCl₃, 400 MHz): chemical shift(ppm) 9.01 (s, 1H), 8.46~8.41 (m, 3H), 8.40 (s, 1H), 8.05 (d, J=8.00 Hz, 1H), 8.00 (d, J=8.00 Hz, 1H), 7.98~7.92 (m, 3H), 7.89~7.84 (m, 3H), 7.79~7.68 (m, 6H), 7.66~7.59 (m, 2H), 7.54~7.49 (m, 3H), 7.42 (s, 1H), 7.39~7.35 (m,2H), 7.30~7.26 (m, 2H), 1.86 (s, 6H).

EXAMPLE 5

Synthesis of Compound A28

Synthesis of 4,4,5,5-tetramethyl-1,3,2-dioxaborolane-10,10-dimethyl-10H-dibenzo[f,h]indeno[1,2-b]quinoline

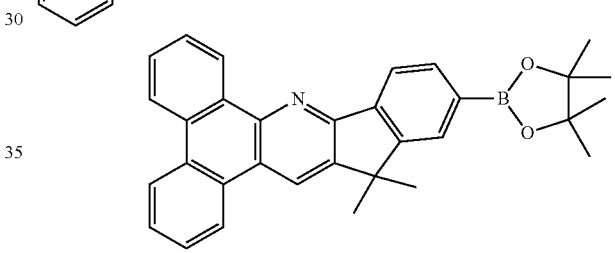

A mixture of 3 g (7 mmol) 12-bromo-10,10-dimethyl-10H-dibenzo[f,h]indeno[1,2-b]quinoline, 2 g (7.9 mmol) of bis(pinacolato)diboron, 0.085 g (0.07 mmol) of Tetrakis(triphenylphosphine)palladium, 2 g (21 mmol) of potassium acetate, and 50 ml 1,4 dioxane was degassed and placed under nitrogen, and then heated at 90° C. for 8 h. After the reaction finish, the mixture was allowed to cool to room temperature. The organic phase separated and washed with ethyl acetate and water. After drying over magnesium sulfate, the solvent was removed in vacuo. The residue was purified by column chromatography on silica (hexane-dichloromethane) to give product (2.4 g, 72%) as a light-yellow solid.

Synthesis of Compound A28

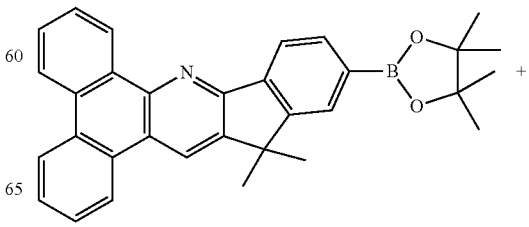

25

-continued

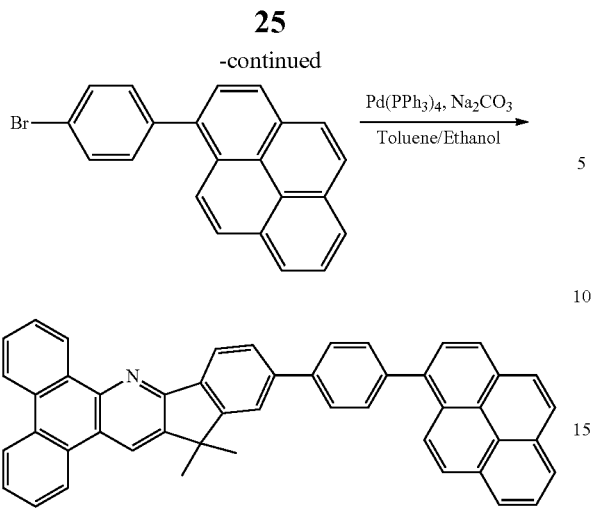

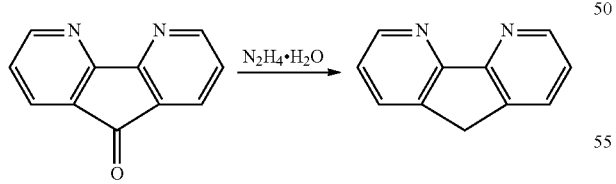

A mixture of 1.8 g (5.1 mmol) of 1-(4-bromophenyl) pyrene, 2.4 g (5.1 mmol) of 4,4,5,5-tetramethyl-1,3,2-dioxaborolane-10,10-dimethyl-10H-dibenzo[f,h]indeno[1,2-b]quinoline, 0.06 g (0.05 mmol) of Tetrakis(triphenylphosphine)palladium, 5 ml of 2M $Na_2CO_3$, 20 ml of EtOH and 60 ml toluene was degassed and placed under nitrogen, and then heated at 90° C. for 24 h. After the reaction finish, the mixture was allowed to cool to room temperature. Than 400 ml MeOH was added, while stirring and the precipitated product was filtered off with suction. To give 1.5 g (yield 48%) of yellow product which was recrystallized from toluene. MS(m/z,FAB+): 621.3; $^1$H NMR ($CDCl_3$, 400 MHz): chemical shift(ppm) 8.62~8.51 (m, 3H), 8.35 (d, J=8.00 Hz, 1H), 8.17 (s, 1H), 8.01~7.84 (m, 8H), 7.79 (d, J=8.00 Hz, 1H), 7.73 (d, J=8.00 Hz, 1H), 7.66~7.56 (m, 5H), 7.32~7.25 (m, 5H), 1.79 (s, 6H).

EXAMPLE 6

Synthesis of Compound A29

Synthesis of 4,5-Diazafluorene

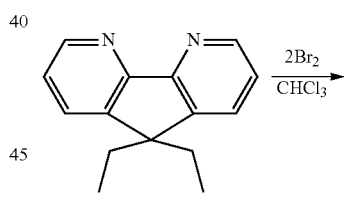

A mixture of 18.2 g (100 mmol) of 4,5-Diazafluoren-9-one, 27 ml (400 mmol) of hydrazine monohydrate, and 500 ml diethylene glycol was degassed and placed under nitrogen, and then heated at 170° C. for 12 h. After the reaction finish, the mixture was allowed to cool to room temperature. The organic layer was extracted with ethyl acetate and water, dried with anhydrous magnesium sulfate, the solvent was removed to give product 15.4 g (91.7%).

26

Synthesis of 5H-Cyclopenta[2,1-:3,4-b']dipyridine, 5,5-diethyl

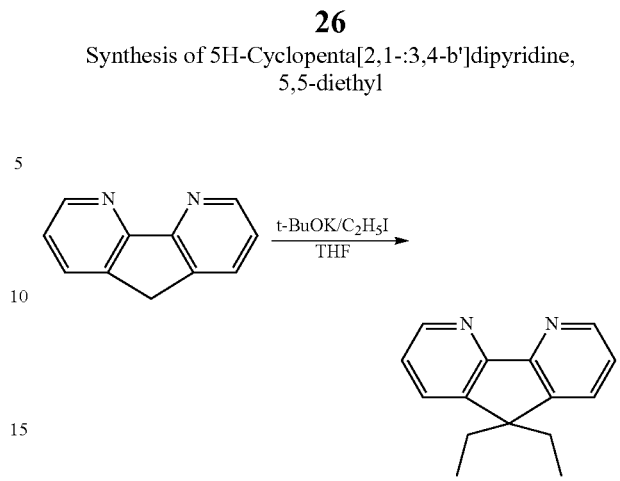

15.4 g (91.6 mmol) of 4,5-Diazafluorene was dissolved in 120 ml dry tetrahydrofuran, and 25.7 g (229 mmol) of potassium tert-butoxide was added to the solution at −10° C. The reaction mixture was maintained at −10° C. for 1 hour. Then the iodoethane 35.7 g (229 mmol) was added dropwise; the solution was then warmed slowly to room temperature and stirred for 6 h. After the reaction completion, water was added to the mixture to terminate the reaction. The reaction mixture was extracted with ethyl acetate and water, dried with anhydrous magnesium sulfate, the solvent was evaporated in vacuo, and the residue was crystallized with toluene to give the 5H-Cyclopenta[2,1-b:3,4-b']dipyridine, 5,5-diethyl-, 15.8 g (76%)

Synthesis of 5H-Cyclopenta[2,1-b:3,4-b']dipyridine, 3,7-dibromo-5,5-diethyl

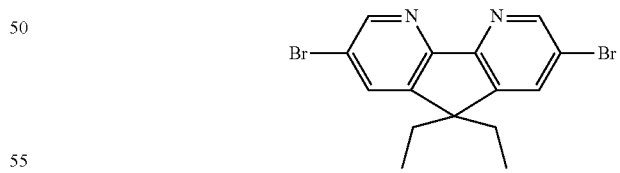

5H-Cyclopenta[2,1-b:3,4-b']dipyridine, 5,5-diethyl- (15 g, 66.9 mmol) was dissolved in chloroform (300 mL), protected from light and bromine (21.9 g, 137 mmol) diluted in chloroform (50 ml) was added drop wise. The mixture was stirred for 24 hours at room temperature, after which water (600 ml) was added, then the precipitated product was filtered off with suction, washed with MeOH and recrystallized from chloroform to give the 5H-Cyclopenta[2,1-b:3,4-b']dipyridine, 3,7-dibromo-5,5-diethyl- 17.1 g (67%)

Synthesis of 2-(biphenyl-2-yl)-7-bromo-5,5-diethyl-5H-Cyclopenta[2,1-b:3,4-b']dipyridine

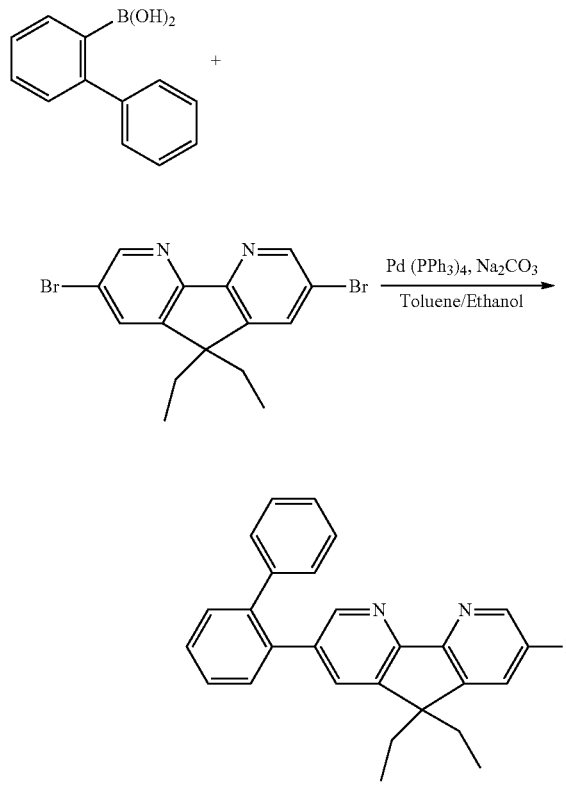

A mixture of 17 g (44.5 mmol) of 5H-Cyclopenta[2,1-b:3,4-b']dipyridine, 3,7-dibromo-5,5-diethy-, 9.7 g (49 mmol) of biphenyl-2-ylboronic acid, 0.5 g (0.445 mmol) of Tetrakis(triphenylphosphine)Palladium, 34 ml of 2M Na₂CO₃, 80 ml of EtOH and 160 ml toluene was degassed and placed under nitrogen, and then heated at 90° C. for 24 h. After the reaction finish, the mixture was allowed to cool to room temperature. The organic layer was extracted with ethyl acetate and water, dried with anhydrous magnesium sulfate, the solvent was removed and the residue was purified by column chromatography on silica (hexane-dichloromethane) to give product (9.7 g, 48%).

Synthesis of 7-dibromo-5,5-diethylpyridine-5H-Cyclopentadibenzo[f,h]quinoline

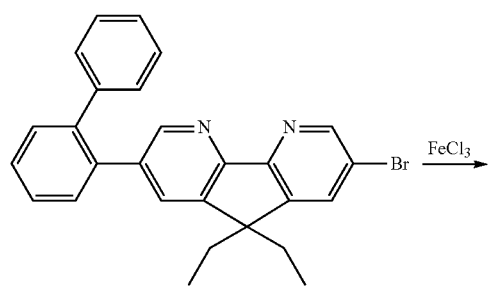

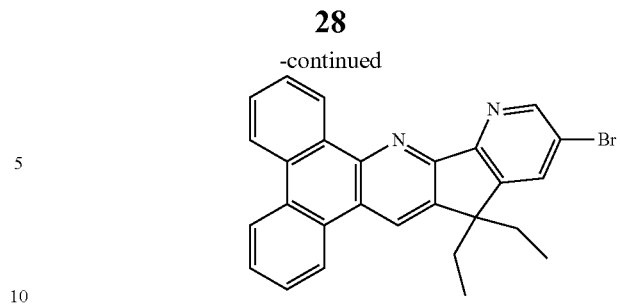

In a 2000 ml three-necked flask that had been deaerated and filled with nitrogen, 9.7 g (21.3 mmol) of 2-(biphenyl-2-yl)-7-bromo-5,5-diethyl-5H-Cyclopenta[2,1-b:3,4-b']dipyridine was dissolved in anhydrous Dichloromethane (600 ml), 34.5 g (213 mmol) Iron(III) chloride was then added, and the mixture was stirred one hour. Methanol 500 ml were added to the mixture and the organic layer was separated and the solvent removed in vacuo. The residue was purified by column chromatography on silica (hexane-dichloromethane) afforded a white solid (3 g, 32%).; ¹H NMR (CDCl₃, 400 MHz): chemical shift(ppm) 8.63~8.50 (m, 5H), 8.24 2.68 (q(s, 1H), 7.99 (d, J=8.00 Hz, 1H), 7.68~7.53 (m, 3H), 7.33 (t, J=8.00 Hz, 1H), J=8.00 Hz, 4H), 0.71 (t, J=6.00 Hz, 6H).

Synthesis of 4,4,5,5-tetramethyl-1,3,2-dioxaborolane-5,5-diethylpyridine-5H-Cyclopentadibenzo[f,h]quinoline

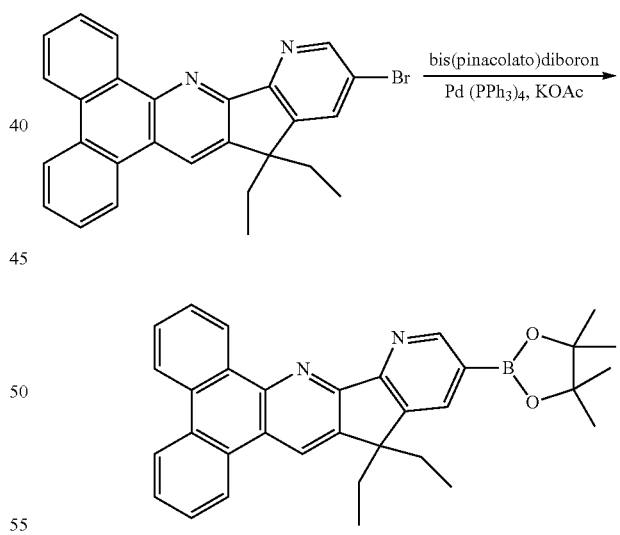

A mixture of 3 g (6.6 mmol) 7-dibromo-5,5-diethylpyridine-5H-Cyclopentadibenzo[f,h]iquinoline, 2 g (7.9 mmol) of bis(pinacolato)diboron, 0.08 g (0.066 mmol) of Tetrakis(triphenylphosphine)Palladium, 1.9 g (19.8 mmol) of potassium acetate, and 50 ml 1,4 dioxane was degassed and placed under nitrogen, and then heated at 90° C. for 16 h. After the reaction finish, the mixture was allowed to cool to room temperature. The organic phase separated and washed with ethyl acetate and water. After drying over magnesium sulfate, the solvent was removed in vacuo. The residue was purified by column chromatography on silica (hexane-dichloromethane) to give product (2.8 g, 84%) as a light-yellow solid.

Synthesis of 10-bromo-9,9'-bianthracene

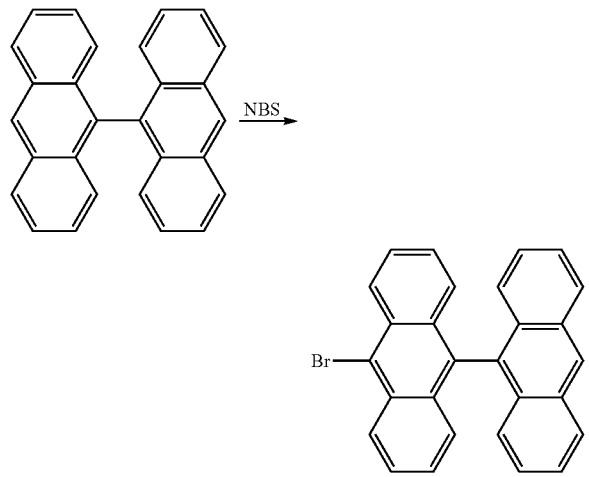

9,9'-bianthracene (10 g, 28.2 mmol) was dissolved in DMF (200 mL), protected from light and N-bromosuccinimide (5.5 g, 31 mmol) diluted in DMF (20 ml) was added to the solution at 0° C. The reaction mixture was maintained at 0° C. for 1 hour. The solution was then warmed slowly to room temperature and stirred for 4 h. After the reaction completion, water was added to the mixture to terminate the reaction. The reaction mixture was extracted with ethyl acetate and water, dried with anhydrous magnesium sulfate, the solvent was removed and the residue was purified by column chromatography on silica(hexane-dichloromethane) to give product 4.5 g (37%) as a yellow solid.

Synthesis of 9,9'-bianthracene-5,5-diethylpyridine-5H-Cyclopentadibenzo[f,h]quinoline

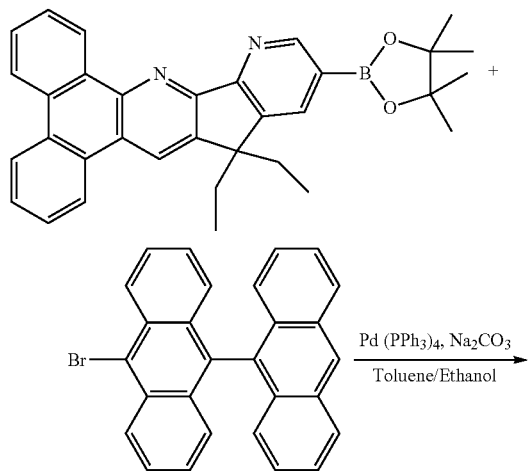

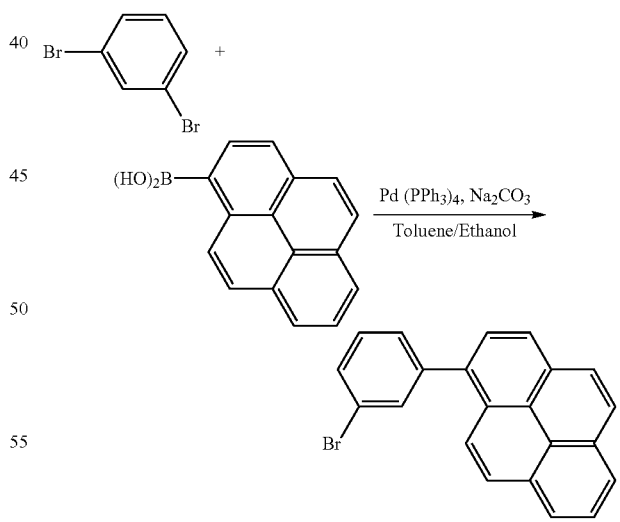

A mixture of 2.4 g (5.6 mmol) of 10-bromo-9,9'-bianthracene, 2.8 g (5.6 mmol) of 4,5,5,5,-tetramethyl-1,3,2-dioxaborolane-5,5-diethylpyridine-5H-Cyclopentadibenzo[f,h]quinoline, 0.06 g (0.056 mmol) of Tetrakis(triphenylphosphine)palladium, 4.2 m; of 2M $Na_2CO_3$, 15 ml of EtOH and 50 ml toluene was degassed and placed under nitrogen, and then heated at 100° C. for 24 h. After the reaction finish, the mixture was allowed to cool to room temperature. Than 100 ml MeOH was added, while stirring and the precipitated product was filtered off with suction. To give 2.6 g (yield 64%) of yellow product which was recrystallized from toluene. MS(m/z,FAB$^+$); 726.3; $^1$H NMR (CDCl$_3$, 400 MHz): chemical shift(ppm) 9.21 (s, 1H), 8.61~8.37 (m, 6H), 7.98 (d, J=8.00 Hz, 1H), 7.93 (d, J=8.00 Hz, 2H), 7.83~7.52 (m, 11H), 7.39~7.19 (m, 7H), 2.62 (q, J=8.00 Hz, 4H), 0.73 (t, J=6.00 Hz, 6H).

EXAMPLE 7

Synthesis of Compound A30

Synthesis of 1-(3-bromophenyl)pyrene

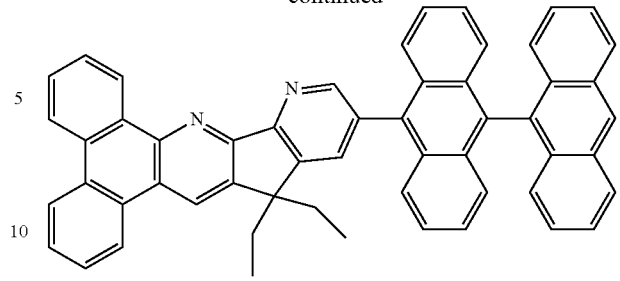

A mixture of 10 g (42.4 mmol) of 1,3-dibromobenzene, 10.43 g (42.4 mmol) of Pyren-1-ylboronic acid, 0.5 g (0.424 mmol) of Tetrakis(triphenylphosphine)palladium, 32 ml of 2M $Na_2CO_3$, 80 ml of EtOH and 160 ml toluene was degassed and placed under nitrogen, and then heated at 90° C. for 24 h. After the reaction finish, the mixture was allowed to cool to room temperature. The organic layer was extracted with ethyl acetate and water, dried with anhydrous magnesium sulfate, the solvent was removed and the residue was purified by column chromatography on silica (hexane-dichloromethane) to give product 7.4 g (49%) as a white solid.

Synthesis of 10,10-dimethyl-12-(3-(pyren-1-yl)phenyl)-10H-indeno[1,2-b]triphenyle

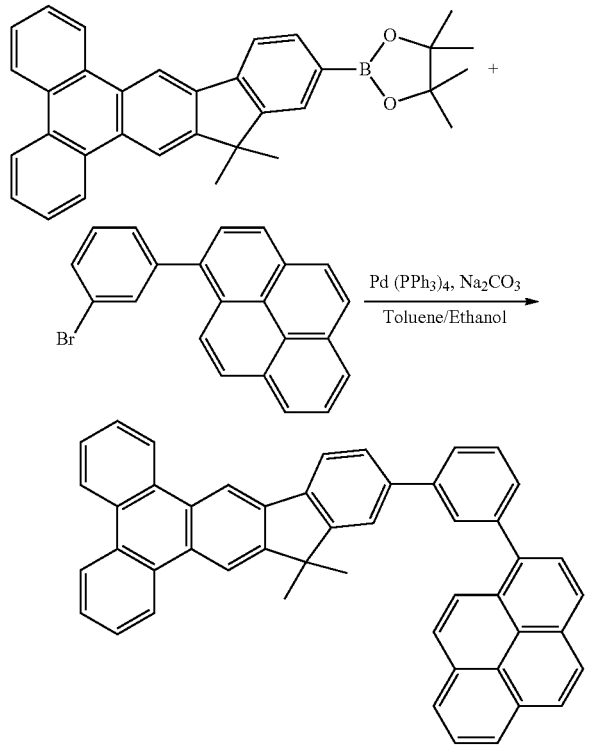

A mixture of 5 g (14 mmol) of 1-(3-bromophenyl)pyrene, 7.53 g (16 mmol) of 2-(10,10-dimethyl-10H-indeno[1,2-b]triphenylen-12-yl)-4,4,5,5-tetramethyl-1,3,2-dioxaborolane, 0.16 g (0.14 mmol) Tetrakis(triphenylphosphine)Palladium, 11 ml of 2M $Na_2CO_3$, 30 ml of EtOH and 65 ml toluene was degassed and placed under nitrogen, and then heated at 90° C. for 12 h. After the reaction finish, the mixture was allowed to cool to room temperature. Than 500 ml MeOH was added, while stirring and the precipitated product was filtered off with suction. To give 4.2 g (yield 49%) of yellow product which was recrystallized from toluene. MS(m/z,$FAB^+$): 620.1; $^1H$ NMR ($CDCl_3$, 400 MHz): chemical shift(ppm) 9.05 (s, 1H), 8.46~8.41 (m, 2H), 8.40 (s, 1H), 8.06~7.84 (m, 9H), 7.74 (d, J=8.00 Hz, 1H), 7.69~7.59 (m, 4H), 7.54~7.39 (m, 5H), 7.31~7.16 (m, 3H), 1.82 (s, 6H).

EXAMPLE 8

Synthesis of Compound A31

Synthesis of 1-(6-bromonaphthalen-2-yl)pyrene

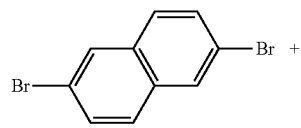

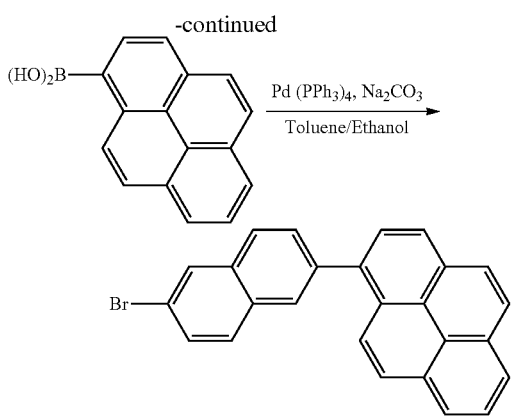

A mixture of 12.1 g (42.4 mmol) of 2,6-dibromonaphthalene, 10.43 g (42.4 mmol) of Pyren-1-ylboronic acid, 0.5 g (0.424 mmol) of Tetrakis(triphenylphosphine)palladium, 32 ml of 2M $Na_2CO_3$, 80 ml of EtOH and 160 ml toluene was degassed and placed under nitrogen, and then heated at 90° C. for 24 h. After the reaction finish, the mixture was allowed to cool to room temperature. The organic layer was extracted with ethyl acetate and water, dried with anhydrous magnesium sulfate, the solvent was removed and the residue was purified, by column chromatography on silica (hexane-dichloromethane) to give product 8.3 g (48%) as a white solid.

Synthesis of 10,10-dimethyl-12-(6-(pyren-1-yl)naphthalen-2-yl)-10H-indeno[1,2-b]triphenylene

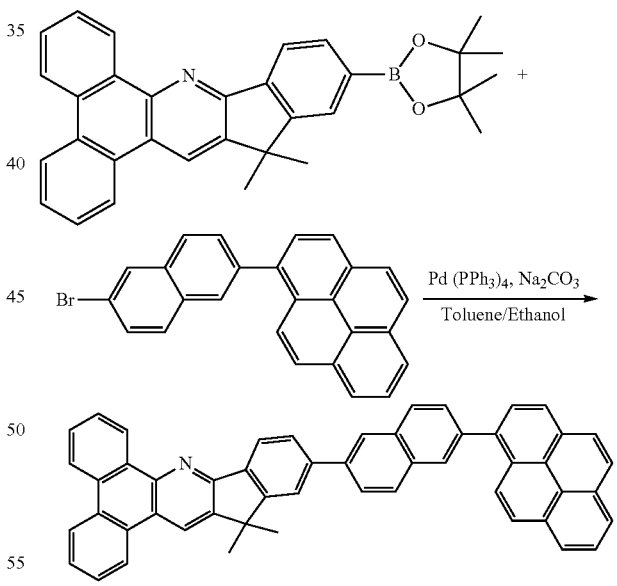

A mixture of 8.3 g (20.3 mmol) of 1-(6-bromonaphthalen-2-yl)pyrene, 9.5 g (20.3 mmol) of 2-(10,10-dimethyl-10H-indeno[1,2-b]triphenylen-12-yl)-4,4,5,5-tetramethyl-1,3,2-dioxaborolane, 0.29 g (0.25 mmol) of Tetrakis(triphenylphosphine)palladium, 17 ml of 2M $Na_2CO_3$, 40 ml of EtOH and 100 ml toluene was degassed and placed under nitrogen, and then heated at 90° C. for 12 h. After the reaction finish, the mixture was allowed to cool to room temperature. Than 500 ml MeOH was added, while stirring and the precipitated product was filtered off with suction. To give 6.3 g (yield 46%) of yellow product which was recrystallized from toluene. MS(m/z,FAB+); 671.5; $^1$H NMR (CDCl$_3$, 400 MHz): chemical shift(ppm) 9.01 (s, 1H), 8.52~8.45 (m, 3H), 8.25 (s, 1H), 8.10~7.89 (m, 9H), 7.78 (d, J=8.00 Hz, 1H), 7.66~7.49 (m, 10H), 7.44 (d, J=8.00 Hz, 1H), 7.28 (d, J=8.00 Hz, 1H), 1.84 (s, 6H).

General Method of Producing Oleds

ITO-coated glasses with 12 ohm/square in Resistance and 120 nm in thickness are provided (hereinafter ITO substrate) and cleaned in a number of cleaning steps in an ultrasonic bath (e.g. detergent, deionized water). Before vapor deposition of the organic layers, cleaned ITO substrates are further treated by UV and ozone. All pre-treatment processes for ITO substrate are under clean room (class 100)

These organic layers are applied onto the ITO substrate in order by vapor deposition in a high-vacuum unit ($10^{-6}$ Torr), such as: resistively heated quartz boats. The thickness of the respective layer and the vapor deposition rate (0.1~0.3 nm/sec) are precisely monitored or set with the aid of a quartz-crystal monitor. It is also possible, as described above, for individual layers to consist of more than one compound, i.e. in general a host material doped with a guest material. This is achieved by co-vaporization from two or more sources.

Dipyrazino[2,3-f:2',3'-h]quinoxaline-2,3,6,7,10,11-hexacarbonitrile (Hat-CN) is used as hole injection layer in this OLEDs. N,N-Bis(naphthalene-1-yl)-N,N'-bis(phenyl)-benzidine (NPB) is most widely used as the hole transporting layer and 2,9-bis(naphthalene-2-yl)-4,7-diphenyl-1,10-phenanthroline (NBphen) is used as electron transporting material in OLEDs for its high thermal stability and long life-time than BPhen/BCP. 9,10-di(naphtha-2-yl)anthrance (AND) and 1,1'-(9,9-dimethyl-9H-fluorene-2,7-diyl)dipyrene (DFDP) is used as emissive host and (E)-6-(4-(diphenylamino)styryl)-N,N-diphenylnaphthalen-2-amine (DPASN) is used as guest. The above OLED materials for producing standard OLEDs in this invention shown its chemical structure as following:

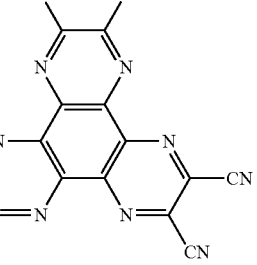

HAT-CN

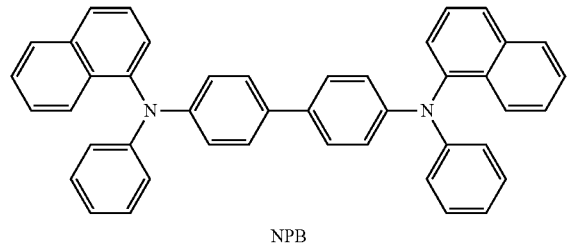

NPB

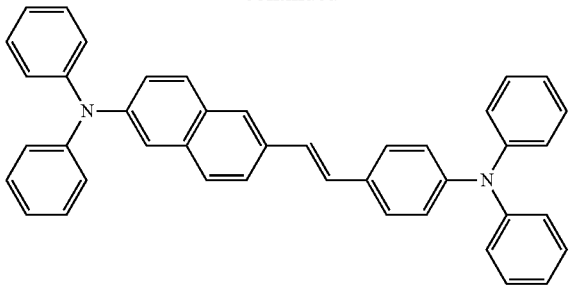

DPASN

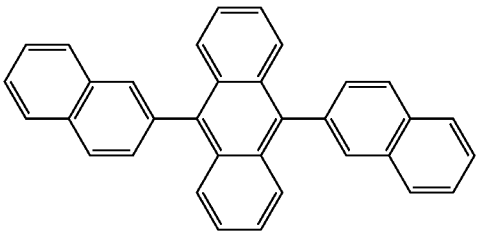

ADN

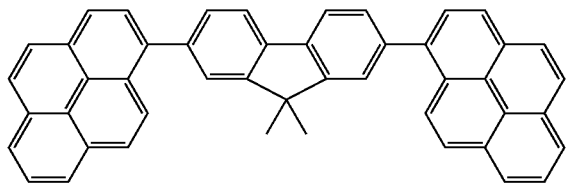

DFDP

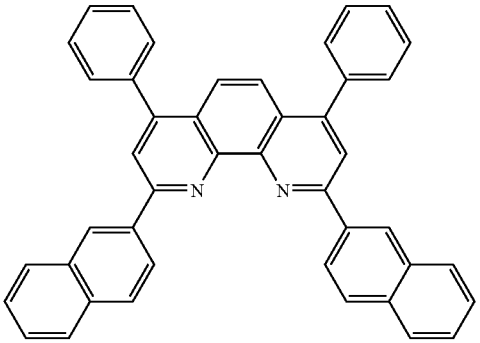

NBphen

A typical OLED consists of low work function metals, such as Al, Mg, Ca, Li and K, as the cathode by thermal evaporation, and the low work function metals can help electrons injecting the electron transporting layer from cathode. In addition, for reducing the electron injection barrier and improving the OLED performance, a thin-film electron injecting layer is introduced between the cathode and the electron transporting layer. Conventional materials of electron injecting layer are metal halide or metal oxide with low work function, such as:

LiF, MgO, or Li$_2$O.

On the other hand, after the OLEDs fabrication, EL spectra and CIE coordination are measured by using a PR650 spectra scan spectrometer. Furthermore, the current/voltage, luminescence/voltage and yield/voltage characteristics are taken with a Keithley 2400 programmable voltage-current source. The above-mentioned, apparatuses are operated at room temperature (about 25° C.) and under atmospheric pressure.

EXAMPLE 9

Using a procedure analogous to the abovementioned general method, fluorescent blue-emitting OLEDs having the following device structure were produced (See FIG. 1):ITO/HAT-CN (20 nm)/NPB (60 nm)/fluorescent blue host doped 5% DPASN (30 nm)/NPhen (30 nm)/LiF (0.5 nm)/Al (160 nm). The I-V-B and half-life time of fluorescent blue-emitting OLED device testing report as Table 1, The half-lifetme is defined that the initial luminance of 3000 cd/m² has dropped to half.

TABLE 1

| fluorescent blue host | Voltage (V) | Luminance (cd/m²) | Yield (cd/A) | CIE (y) | Half-lifetime (hour) Initial luminance = 3000 (cd/m²) |
|---|---|---|---|---|---|
| Compound A12 | 5 | 1020 | 4.61 | 0.157 | 850 |
| Compound A13 | 5 | 615 | 4.44 | 0.148 | 920 |
| Compound A15 | 5 | 721 | 5.22 | 0.160 | 750 |
| Compound A27 | 5 | 619 | 5.30 | 0.145 | 350 |
| Compound A28 | 5 | 1100 | 4.48 | 0.156 | 310 |
| Compound A29 | 5 | 269 | 3.35 | 0.163 | 150 |
| Compound A30 | 5 | 1090 | 4.72 | 0.160 | 860 |
| Compound A31 | 5 | 697 | 5.16 | 0.145 | 330 |
| DFDP | 5 | 276 | 4.08 | 0.158 | 260 |
| ADN | 5 | 557 | 2.31 | 0.185 | 200 |

In the above preferred embodiments, we show that indenotriphenylene derivatives used as fluorescent blue host than comparable example DFDP and ADN with higher half-life time and practical operation durability. Higher luminance than comparable DFDP and ADN has also been achieved at a driving voltage of 5V using the mentioned new indenotriphenylene derivatives for blue-emitting organic electroluminescent devices. The efficiency of all present invention examples show over 4 cd/A and appears CIE(y) are between 0/14 and 0.16. The indenotriphenylene derivatives can be used as fluorescent blue host.

To sum up, the present invention discloses a indenotriphenylene derivatives which can be used for OLEDs is disclosed. The mentioned indenotriphenylene derivatives are represented by the following formula(A).

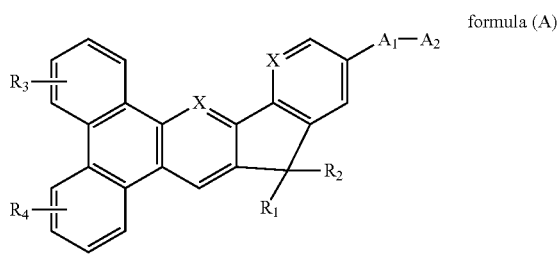

formula (A)

according to the formula(A), $A_1$, $A_2$ are substituted or unsubstituted aromatic ring systems with one to five rings and independently selected from the group consisting of a phenyl group, a naphthyl group, an anthracenyl group, a pyrenyl group, a chrysenyl group and a perylenyl group. $R_1$ to $R_4$ are identical or different. $R_1$ to $R_4$ are independently selected from the group consisting of a hydrogen atom, a halide, an alkyl group having 1 to 20 carbon atoms, a substituted or unsubstituted aryl group having 6 to 30 carbon atoms, a substituted or unsubstituted aralkyl group having 6 to 30 carbon atoms and a substituted or unsubstituted heteroaryl group having 6 to 30 carbon atoms. X is selected from carbon atom or nitrogen atom.

Obvious many modifications and variations are possible in light of the above teachings. It is therefore to be understood that within the scope of the appended claims the present invention can be practiced otherwise than as specifically described herein. Although specific embodiments have been illustrated and described herein, it is obvious to those skilled in the art that many modifications of the present invention may be made without departing from what is intended to be limited solely by the appended claims.

The invention claimed is:

1. A new indenotriphenylene derivative is represented by the following formula(A):

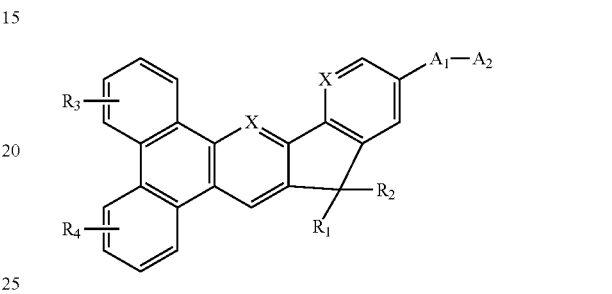

wherein $A_1$, $A_2$ are substituted or unsubstituted aromatic ring systems with one to five rings and independently selected from the group consisting of a phenyl group, a naphthyl group, an anthracenyl group, a pyrenyl group, a chrysenyl group, and a perylenyl group, $R_1$ to $R_4$ are identical or different and independently selected from the group consisting of a hydrogen atom, a halide, an alkyl group having 1 to 20 carbon atoms, a substituted or unsubstituted aryl group having 6 to 30 carbon atoms, a substituted or unsubstituted aralkyl group having 6 to 30 carbon atoms and a substituted or unsubstituted heteroaryl group having 6 to 30 carbon atoms, and X is selected from carbon atom or nitrogen atom.

2. The compound as claimed in claim 1, wherein both of X are nitrogen atoms, and the compound is represented by the following formula(aI):

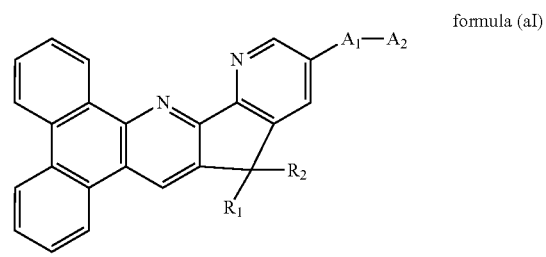

formula (aI)

wherein $A_1$, $A_2$ are substituted or unsubstituted aromatic ring systems with one to five rings and independently selected from the group consisting of a phenyl group, a naphthyl group, an anthracenyl group, a pyrenyl group, a chrysenyl group and a perylenyl group, $R_1$ to $R_4$ are identical or different and independently selected from the group consisting of a hydrogen atom, a halide, an alkyl group having 1 to 20 carbon atoms, a substituted or unsubstituted aryl group having 6 to 30 carbon atoms, a substituted or unsubstituted aralkyl group having 6 to 30 carbon atoms and a substituted or unsubstituted heteroaryl group having 6 to 30 carbon atoms.

3. The compound as claimed in claim 1, wherein both of X are carbon atoms, and the compound is represented by the following formula(aII):

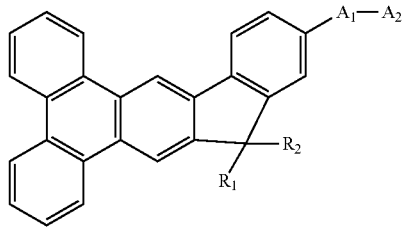

formula (aII)

wherein $A_1$, $A_2$ are substituted or unsubstituted aromatic ring systems with one to five rings and independently selected from the group consisting of a phenyl group, a naphthyl group, an anthracenyl group, a pyrenyl group, a chrysenyl group and a perylenyl group, $R_1$ to $R_4$ are identical or different and independently selected from the group consisting of a hydrogen atom, a halide, an alkyl group having 1 to 20 carbon atoms, a substituted or unsubstituted aryl group having 6 to 30 carbon atoms, a substituted or unsubstituted aralkyl group having 6 to 30 carbon atoms and a substituted or unsubstituted heteroaryl group having 6 to 30 carbon atoms.

4. The compound as claimed in claim 1, one of X is a carbon atom and another X is a nitrogen atom, and the compound is represented by the following formula(aIII):

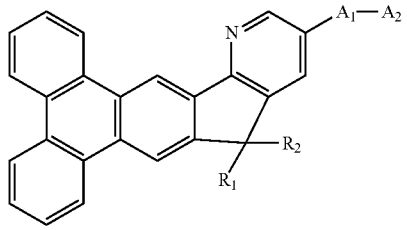

formula (aIII)

wherein $A_1$, $A_2$ are substituted or unsubstituted aromatic ring systems with one to five rings and independently selected from the group consisting of a phenyl group, a naphthyl group, an anthracenyl group, a pyrenyl group, a chrysenyl group and a perylenyl group, $R_1$ to $R_4$ are identical or different and independently selected from the group consisting of a hydrogen atom, a halide, an alkyl group having 1 to 20 carbon atoms, a substituted or unsubstituted aryl group having 6 to 30 carbon atoms, a substituted or unsubstituted aralkyl group having 6 to 30 carbon atoms and a substituted or unsubstituted heteroaryl group having 6 to 30 carbon atoms.

5. The compound as claimed in claim 1, one of X is a carbon atom and another X is a nitrogen atom, and the compound is represented by the following formula(aIV):

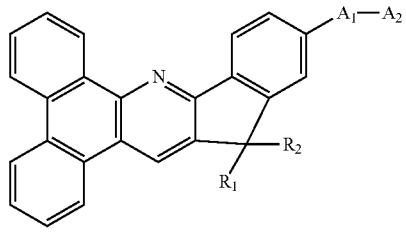

formula (aIV)

wherein $A_1$, $A_2$ are substituted or unsubstituted aromatic ring systems with one to five rings and independently selected from the group consisting of a phenyl group, a naphthyl group, an anthracenyl group, a pyrenyl group, a chrysenyl group and a perylenyl group, $R_1$ to $R_4$ are identical or different and independently selected from the group consisting of a hydrogen atom, a halide, an alkyl group having 1 to 20 carbon atoms, a substituted or unsubstituted aryl group having 6 to 30 carbon atoms, a substituted or unsubstituted aralkyl group having 6 to 30 carbon atoms and a substituted or unsubstituted heteroaryl group having 6 to 30 carbon atoms.

6. The compound as claimed in claim 1, $A_1$ are represented by the following ring hydrocarbon units:

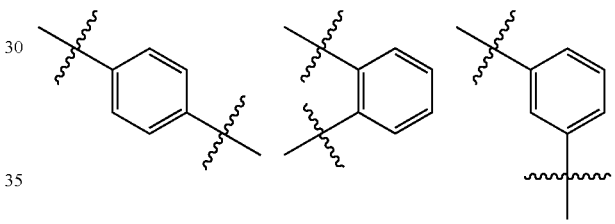

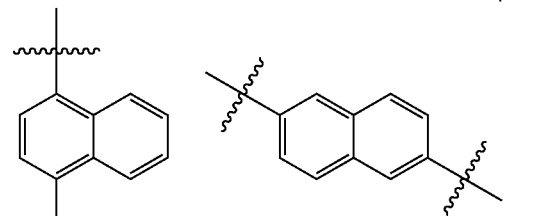

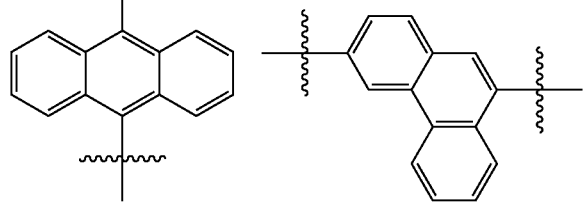

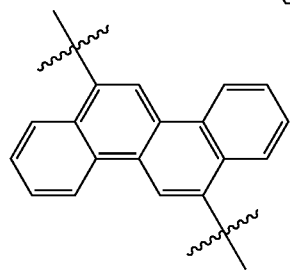

-continued

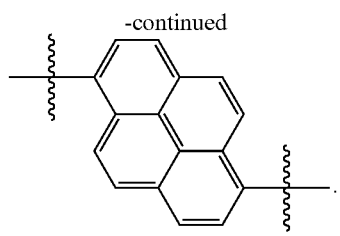

7. The compound as claimed in claim 1, $A_2$ are represented by the following ring hydrocarbon units:

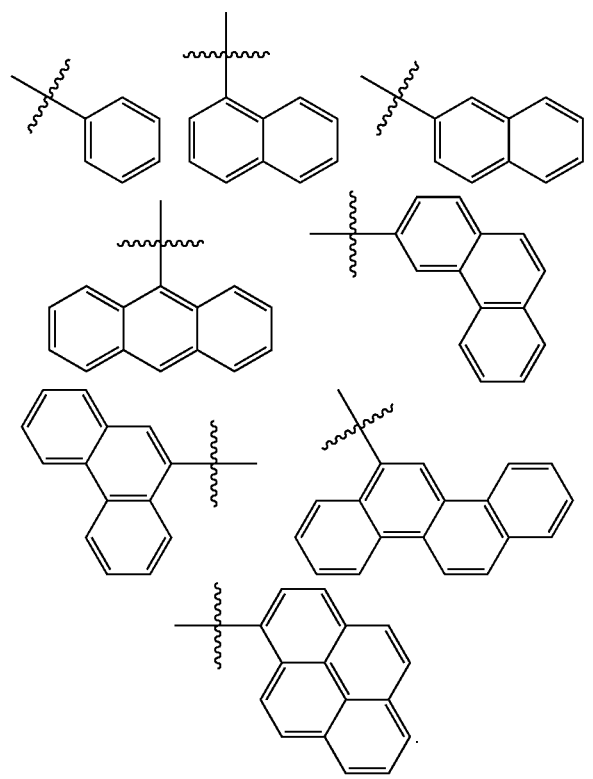

8. A organic light emitting device comprising a pair of electrodes consisting of a cathode and an anode and between the pairs of electrodes comprising a layer of indenotriphenylene derivatives represented as the following formula(A):

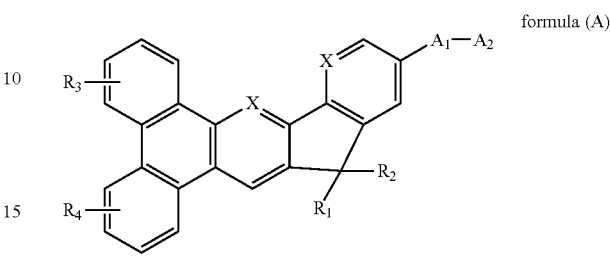

formula (A)

wherein $A_1$, $A_2$ are substituted or unsubstituted aromatic ring systems with one to five rings and independently selected from the group consisting of a phenyl group, a naphthyl group, an anthracenyl group, a pyrenyl group, a chrysenyl group and a perylenyl group, $R_1$ to $R_4$ are identical or different and independently selected from the group consisting of a hydrogen atom, a halide, an alkyl group having 1 to 20 carbon atoms, a substituted or unsubstituted aryl group having 6 to 30 carbon atoms, a substituted or unsubstituted aralkyl group having 6 to 30 carbon atoms and a substituted or unsubstituted heteroaryl group having 6 to 30 carbon atoms.

9. According to claim 8, an organic light emitting device comprising a layer of indenotriphenylene derivatives and functions as host material of a light emitting layer.

10. According to claim 8, an organic light emitting device comprising a layer of indenotriphenylene derivatives and functions as blue emitting host material of a light emitting layer.

* * * * *